(12) United States Patent
Mohseni et al.

(10) Patent No.: US 9,995,701 B2
(45) Date of Patent: Jun. 12, 2018

(54) CAPACITIVE SENSING APPARATUSES, SYSTEMS AND METHODS OF MAKING SAME

(71) Applicant: CASE WESTERN RESERVE UNIVERSITY, Cleveland, OH (US)

(72) Inventors: Pedram Mohseni, Cleveland, OH (US); Michael A. Suster, Cleveland, OH (US); Mehran Bakshiani, Cleveland, OH (US); Umut Gurkan, Cleveland, OH (US)

(73) Assignee: Case Western Reserve University, Cleveland, OH (US)

( * ) Notice: Subject to any disclaimer, the term of this patent is extended or adjusted under 35 U.S.C. 154(b) by 222 days.

(21) Appl. No.: 14/728,642

(22) Filed: Jun. 2, 2015

(65) Prior Publication Data

US 2015/0346131 A1 Dec. 3, 2015

Related U.S. Application Data

(60) Provisional application No. 62/006,560, filed on Jun. 2, 2014.

(51) Int. Cl.
*G01R 27/08* (2006.01)
*G01N 27/22* (2006.01)
*G01N 27/02* (2006.01)

(52) U.S. Cl.
CPC ......... *G01N 27/221* (2013.01); *G01N 27/026* (2013.01); *Y10T 29/49156* (2015.01)

(58) Field of Classification Search
CPC ........ G01R 15/02; G01R 15/08; G01R 15/09; G01R 15/125; G01R 1/458; G01R 1/6705; G01R 1/28
See application file for complete search history.

(56) References Cited

U.S. PATENT DOCUMENTS 4,686,857 A * 8/1987 Kato ..................... G01N 27/06
324/698
4,884,457 A * 12/1989 Hatton .................... G01F 1/708
738/861.04

(Continued)

FOREIGN PATENT DOCUMENTS

WO 2010109317 A1 9/2010
WO 2014141845 A1 9/2014
WO 2016040490 A1 3/2016

OTHER PUBLICATIONS

Mohseni, Pedram, et al., A Miniaturized Dielectric Blood Coagulometer:, Oct. 20, 2015.

(Continued)

*Primary Examiner* — Tung X Nguyen
*Assistant Examiner* — Dominic Hawkins
(74) *Attorney, Agent, or Firm* — Tarolli, Sundheim, Covell & Tummino LLP

(57) ABSTRACT

A sensor system can be configured to perform dielectric spectroscopy (DS). For example, the system can include a sensor configured to measure dielectric permittivity of a fluid in response to an RF input signal. Associated interface electronics can include a transmitter to drive the sensor with the RF input signal and a receiver to receive and process an RF output signal from the sensor in response to the RF input signal.

25 Claims, 12 Drawing Sheets

(56) References Cited

U.S. PATENT DOCUMENTS

| | | | | |
|---|---|---|---|---|
| 5,042,299 | A * | 8/1991 | Wells | G01F 23/268 324/663 |
| 5,558,086 | A * | 9/1996 | Smith | A61M 16/00 128/204.23 |
| 6,255,954 | B1 * | 7/2001 | Brown | B41J 2/01 324/698 |
| 6,362,632 | B1 * | 3/2002 | Livingston | G01F 23/266 324/629 |
| 6,467,358 | B1 * | 10/2002 | Nishi | G01F 1/363 73/861.04 |
| 6,922,064 | B2 | 7/2005 | Halalay et al. | |
| 7,541,004 | B2 | 6/2009 | Niksa et al. | |
| 8,735,163 | B2 | 5/2014 | Hayashi et al. | |
| 8,776,246 | B2 | 7/2014 | Allegri et al. | |
| 8,884,771 | B2 * | 11/2014 | Cooke | G08B 17/10 340/603 |
| 9,194,859 | B2 | 11/2015 | Emeric et al. | |
| 2003/0090276 | A1 * | 5/2003 | Weide | G01N 22/00 324/663 |
| 2004/0237657 | A1 | 12/2004 | Xie et al. | |
| 2010/0235107 | A1 * | 9/2010 | Fukumura | G01N 27/226 702/24 |
| 2010/0251816 | A1 * | 10/2010 | Bahorich | G01F 23/266 73/304 C |
| 2010/0252452 | A1 | 10/2010 | Newman et al. | |
| 2011/0234240 | A1 | 9/2011 | Yager | |
| 2012/0055810 | A1 * | 3/2012 | Zhou | G01N 17/02 205/775.5 |
| 2012/0112850 | A1 * | 5/2012 | Kim | H03H 7/38 333/32 |
| 2012/0238026 | A1 | 9/2012 | Hayashi et al. | |
| 2013/0204202 | A1 * | 8/2013 | Trombly | A61M 5/16877 604/207 |
| 2013/0296847 | A1 * | 11/2013 | Germain | A61B 18/1206 606/39 |
| 2014/0114592 | A1 * | 4/2014 | Eilertsen | G01R 31/028 702/58 |
| 2015/0346125 | A1 | 12/2015 | Hayashi et al. | |
| 2015/0346131 | A1 | 12/2015 | Mohseni et al. | |
| 2016/0011170 | A1 | 1/2016 | Brun | |

OTHER PUBLICATIONS

Hamed Mazhab-Jafari,et al., "16-Channel CMOS Impedance Spectroscopy DNA Analyzer With Dual-Slope Multiplying ADCs", IEEE Transactions on Biomedical Circuits and Systems, vol. 6, No. 5, Oct. 2012, pp. 468-478.

Osama Elhadidy, et al., "A CMOS Fractional- PLL-Based Microwave Chemical Sensor With 1.5% Permittivity Accuracy" IEEE Transactions on Microwave Theory and Techniques, vol. 61, No. 9, Sep. 2013, pp. 3402-3416.

Jun-Chau Chien, et al., "A 1-50 GHz Dielectric Spectroscopy Biosensor with Integrated Receiver Front-end in 65nm CMOS", 2013.

Ahmed A. Helmy, et al., "A 1-8-GHz Miniaturized Spectroscopy System for Permittivity Detection and Mixture Characterization of Organic Chemicals", IEEE Transactions on Microwave Theory and Techniques, vol. 60, No. 12, Dec. 2012, pp. 4157-4170.

Ahmed A. Helmy, et al., "Complex Permittivity Detection of Organic Chemicals and Mixtures Using a 0.5-3-GHz Miniaturized Spectroscopy System", IEEE Transactions on Microwave Theory and Techniques, vol. 51, No. 12, Dec. 2013, pp. 4646-4659.

Masoud Moslehi Bajestan, et al., "A 0.62-1 OGHz CMOS Dielectric Spectroscopy System for Chemical/Biological Material Characterization", 2014.

Jun-Chau Chien, et al., "A 6.5/11117.S/30-GHz High Throughput Interferometer-based Reactance Sensors using Injection-Locked Oscillators and Ping-Pong Nested Chopping", 2014 Symposium on VLSI Circuits Digest of Technical Papers.

Mehran Bakhshiani, et al., "A Microfluidic-CMOS Platform with 3D Capacitive Sensor and Fully Integrated Transceiver IC for Palmtop Dielectric Spectroscopy", 2015 IEEE International Solid-State Circuits Conference, pp. 386-388.

Mehran Bakhshiani, et al., "A 9 MHz-2.4 GHz Fully Integrated Transceiver IC for a Microfluidic-CMOS Platform Dedicated to Miniaturized Dielectric Spectroscopy", IEEE Transactions on Biomedical Circuits and Systems, vol. 9, No. 6, Dec. 2015, pp. 849-861.

Michael A. Suster, et al., "An RF/Microwave Microfluidic Sensor Based on a 3D Capacitive Structure with a Floating Electrode for Miniaturized Dielectric Spectroscopy", 2014.

Osama Elhadidy, et al., "A Wide-Band Fully-Integrated CMOS Ring-Oscillator PLL-Based Complex Dielectric Spectroscopy System", IEEE Transactions on Circuits and Systems—I: Regular Papers, vol. 62, No. 8, Aug. 2015, pp. 1940-1949.

Michael A. Suster, et al., "A Circuit Model of Human Whole Blood in a Microfluidic Dielectric Sensor", IEEE Transactions on Circuits and Systems—II: Express Briefs, vol. 63, No. 12, Dec. 2016, pp. 1156-1160.

S. Gawad, et al., "Micromachined impedance spectroscopy flow cytometer for cell analysis and particle sizing", Lab on a Chip, 2001, 1, pp. 76-82.

Ahmet C. Sabuncu, et al., "Microfluidic impedance spectroscopy as a tool for quantitative biology and biotechnology", Biomicrofluidics 6, 034103 (2012).

Michael A. Suster, et al., "An RF/Microwave Microfluidic Sensor Based on a Center-Gapped Microstrip Line for Miniaturized Dielectric Spectroscopy", 2013.

Mehran Bakhshiani, et al., "A Broadband Sensor Interface IC for Miniaturized Dielectric Spectroscopy From MHz to GHz", IEEE Journal of Solid-State Circuits, vol. 49, No. 8, Aug. 2014.

S S Stuchly, et al., "Microwave coplanar sensors for dielectric measurements", Meas. Sci. Technol. 9 (1998) pp. 1324-1329.

Michael A. Suster, et al., "An RF/Microwave Microfluidic Sensor for Miniaturized Dielectric Spectroscopy Based on Sensor Transmission Characteristics", 2015.

G. R. Facer, et al., "Dielectric spectroscopy for bioanalysis: From 40 Hz to 26.5 GHz in a microfabricated wave guide", Applied Physics Letters, vol. 78, No. 7, Feb. 12, 2001, pp. 996-998.

Milan Daphtary, et al., "Broadband Capacitive Sensor CMOS Interface Circuit for Dielectric Spectroscopy", ISCAS 2006, pp. 4285-4288.

Sanghyun Seo, et al., "High Frequency Wideband Permittivity Measurements of Biological Substances Using Coplanar Waveguides and Application to Cell Suspensions", 2008, pp. 915-918.

Khalil Heileman, et al., "Dielectric spectroscopy as a viable biosensing tool for cell and tissue characterization and analysis", Biosensors and Bioelectronics, 49 (2013), pp. 348-359.

Ebrahim Ghafar-Zadeh, et al., "A Hybrid Microfluidic/CMOS Capacitive Sensor Dedicated to Lab-on-Chip Applications", IEEE Transactions on Biomedical Circuits and Systems, vol. 1, No. 4, Dec. 2007, pp. 270-277.

Chao Yang, et al., "Compact Low-Power Impedance-to-Digital Converter for Sensor Array Microsystems", IEEE Journal of Solid-State Circuits, vol. 44, No. 10, Oct. 2009, pp. 2844-2855.

Katia Grenier, et al., "Integrated Broadband Microwave and Microfluidic Sensor Dedicated to Bioengineering", IEEE Transactions on Microwave Theory and Techniques, vol. 57, No. 12, Dec. 2009, pp. 3246-3253.

Arun Manickam, et al., "A CMOS Electrochemical Impedance Spectroscopy (EIS) Biosensor Array", IEEE Transactions on Biomedical Circuits and Systems, vol. 4, No. 6, Dec. 2010, pp. 379-390.

Ahmed A. Helmy, et al., "A Self-Sustained CMOS Microwave Chemical Sensor Using a Frequency Synthesizer", IEEE Journal of Solid-State Circuits, vol. 47, No. 10, Oct. 2012, pp. 2467-2483.

James C. Booth, et al., "Quantitative Permittivity Measurements of Nanoliter Liquid Volumes In Microfluidic Channels to 40 GHz", IEEE Transactions on Instrumentation and Measurement, vol. 59, No. 12, Dec. 2010, pp. 3279-3288.

Kang-Ho Lee, et al., "A CMOS Impedance Cytometer for 3D Flowing Single-Cell Real-Time Analysis ?S with Error Correction", 2012 IEEE International Solid-State Circuits Conference, pp. 304-306.

* cited by examiner

CAPACITIVE SENSING APPARATUSES, SYSTEMS AND METHODS OF MAKING SAME

CROSS REFERENCE TO RELATED APPLICATION

This application claims the benefit of priority from U.S. Provisional Patent application No. 62/006,560, filed Jun. 2, 2015, and entitled SENSOR APPARATUS, SYSTEM AND METHODS OF MAKING AND USING SAME, which is incorporated herein by reference in its entirety.

TECHNICAL FIELD

This disclosure relates to a sensor apparatus, to systems, to methods of making a sensor and to methods of using a sensor for spectroscopy.

BACKGROUND

Quantitative measurement of the complex dielectric permittivity of a material versus frequency (e.g., dielectric spectroscopy, also known as DS) can be a powerful monitoring technique with a broad range of applications. For example, DS can be utilized for chemical analysis of oil in the petroleum industry, analysis of substances for security or defense purposes, soil moisture monitoring in agriculture, fermentation monitoring during the production of alcoholic beverages, food quality/safety monitoring and drug development in the pharmaceutical industry. DS can also be used as an analytical tool in the biomedical field as a label-free, non-destructive and real-time method to study the interaction of RF/microwave fields with biological/biochemical samples with minimal sample preparation. Key molecular characteristics of biomaterials such as human blood, spinal fluid, breast tissue and skin have been studied using DS for applications in disease detection and clinical diagnosis. Typical DS systems tend to be large and expensive, making them cost-prohibitive in certain circumstances.

SUMMARY

This disclosure relates to a sensor system, to methods of making a sensor and to methods of using a sensor.

As one example, a sensor includes an input configured to receive an input radio frequency (RF) signal and an output to provide an output RF signal. The sensor also includes a capacitive sensor comprising substantially co-planar sensing electrodes, a first of the sensing electrodes being coupled to the input and a second of the sensing electrode coupled to the output. The capacitive sensor also including a floating electrode spaced apart from the sensing electrodes by a space that defines a fluid channel that is communicatively coupled to receive a fluid material via the fluid port.

As another example, a portable dielectric spectroscopy system may include an integrated sensor interface system comprising a transmitter and a receiver. The transmitter is configured to generate and provide a radio frequency (RF) excitation signal to an output for exciting a capacitive sensor containing a fluid material under test. The receiver is coupled to at least one input to receive an input RF signal and to provide at least one system signal representing measured transmission characteristics of the capacitive sensor in response to the excitation signal. A computing system is programmed to calculate a dielectric permittivity of the material fluid within the channel based on the at least one system signal.

As another example, a method of fabricating a sensor can include forming substantially planar sensor electrodes on a first substrate to provide a first part of the sensor. An electrically conductive trace extends from at least one of the sensor electrodes to a termination. The method also includes forming a floating electrode on a wall of a second substrate to provide a second part of the sensor, a space between the floating electrode and the at least one sensor electrode defining a capacitive sensing area within a fluid channel that extends from an opening extending from a surface of the second substrate to the recessed wall. The method also includes attaching the first and second parts of the sensor such that the sensor electrodes are spaced apart from and opposing the floating electrode by a gap to form the fluid channel therebetween.

DETAILED DESCRIPTION

This disclosure relates to a sensor system, to a method of making a sensor and to a method of using a sensor. The sensor and associated interface electronics can be implemented in a miniaturized platform (e.g., a microsystem) to perform dielectric spectroscopy (DS). For example, the sensor can be a microfluidic sensor configured to measure dielectric permittivity of a fluid (e.g., a liquid (e.g., solution) or a gas). The associated interface electronics can include a transmitter to drive the sensor with an RF input signal and a receiver to receive an RF output signal from the sensor. The interface electronics can be programmable to adjust performance and sensitivity of the sensor for a wide range of sensing applications. A computing system (e.g., including microprocessor and memory) can be integrated into the DS system for control and data processing to derive DS information, including to calculate permittivity for a material under test. The derived information and acquired sensor data can be communicated via a communication link to a remote device, such as for display of the DS information.

The DS system can be implemented in a palmtop platform for miniaturized DS, such as in the MHz-to-GHz range. The DS sensor disclosed herein can be implemented as microfluidic sensor that includes a three-dimensional, parallel-plate, capacitive structure for extracting complex permittivity of µL-volume materials under test (MUTs). The integrated platform thus can achieve accurate measurement of real and imaginary parts of complex permittivity of MUTs with measurement time of a few seconds or faster. As a result, the approach disclosed herein provides rapid, high-throughput, low-cost DS measurements with a self-sustained, low-power, portable instrument.

Figure 1:
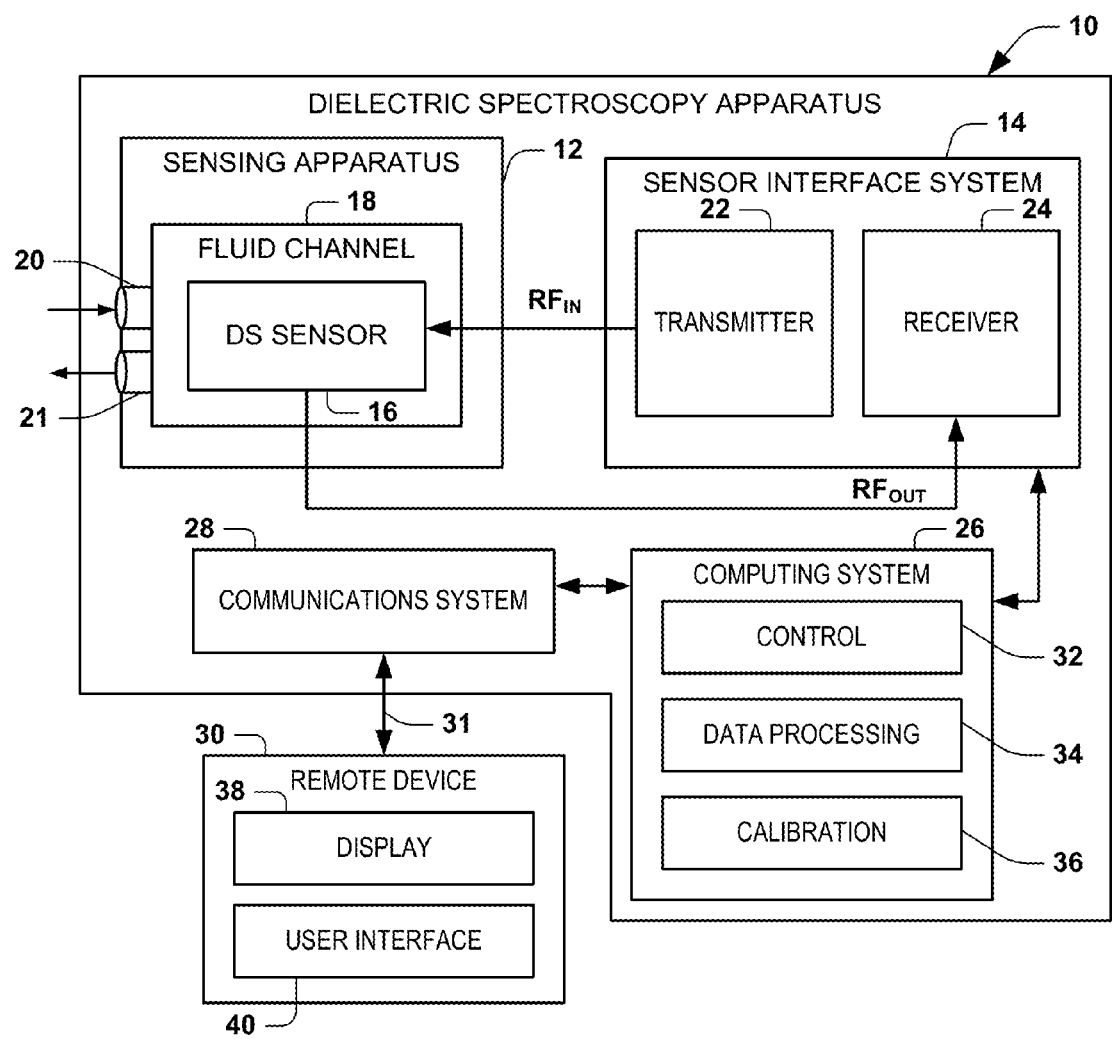
FIG. 1 depicts an example of a system to measure dielectric permittivity.

FIG. 1 depicts an example of a system 10 to measure dielectric permittivity. The system 10 can include a sensing apparatus 12 and a sensor interface system 14. The sensor interface system 14 can drive DS sensor circuitry 16 with an RF input signal ($RF_{IN}$). The DS sensor circuitry 16 resides in a fluid channel 18 and is configured to have a dielectric permittivity that depends on fluid that is within the fluid channel 18. For example, a fluid MUT can be provided (e.g., from a source of fluid, such as a micropipette) into the fluid channel 18 via one or more fluid ports 20. The fluid can be substantially still within the channel or it can be flowing through the channel during measurements. The fluid channel can be a microfluidic channel.

As disclosed herein, the DS sensor 16 can include electrodes distributed in the channel 18 in an opposing relationship as to provide a capacitive sensing area between opposing surfaces of the electrodes. For example, a floating electrode can be fixed with respect to a surface of the fluid channel in a spaced apart opposing relationship from a pair of sensing electrodes fixed with respect to another surface of the channel. The pair of sensing electrodes thus can be substantially coplanar along a given surface of the fluid channel 18 that opposes and is parallel to the floating electrode. One of the sensing electrodes can be configured to receive the RF input signal as an excitation signal and the other sensing electrodes can provide a corresponding RF output signal ($RF_{OUT}$).

The sensor interface system 14 can include a transmitter 22 and a receiver 24. The transmitter 22 can be configured to provide the RF input signal at a desired excitation frequency. The excitation frequency, for example, can be in the microwave range. For instance the transmitter 22 can provide the RF input signal in a range from about 1 MHz to about 100 GHz (e.g., from about 5 MHz to about 10 GHz). The excitation frequency can be set in response to a program input signal (e.g., by a user input via remote device 30), such as to vary the frequency according to application requirements. The frequency range for the excitation signal can be continuous across the range or be provided in two or more discrete frequency bands (see, e.g., FIG. 11), which can be user programmable.

The receiver 24 is configured to provide an output signal (OUT) representing measured sensor transmission characteristics based on the RF output signal from each DS sensor implemented in the sensing apparatus 12. The output signal can be an analog signal or a digital signal. The receiver 24 can include circuitry configured to process the RF output signal, such as by amplifying (e.g., variable gain) and filtering the RF output signal to ascertain complex signal components of the RF output signal, which filtering can be configured according to the frequency range of the excitation signal. The RF output signal can be a complex signal corresponding to voltage transmission measurements through the DS sensor 16, which varies as a function of the complex impedance or admittance as seen at an output node thereof (e.g., demonstrated at $RF_{OUT}$ in various figures herein). That is, the RF output signal can have a predetermined relationship with respect to a change in dielectric permittivity caused by the MUT within the channel 18.

The transmitter 22 and receiver 24 can be implemented in an integrated circuit chip (e.g., system on chip) or they could be implemented as separate components configured to perform the functions disclosed herein. While the transmitter 22 and receiver 24 are demonstrated in FIG. 1 as co-residing in the interface system 14 (e.g., in a single IC chip), in other examples, the transmitter and receiver could be implemented as independent separate circuits.

In the example of FIG. 1, the DS apparatus 10 also includes a computing system 26. The computing system 26 can be configured (e.g., including a processing unit and memory to store instructions and data) to implement DS control 32 to control operating the sensor interface system 14. For example, the DS control 32 can selectively control the range of frequencies (e.g., frequency bands) of an RF output signal applied by the transmitter 22 to each respective DS sensor 16. As mentioned, the transmitter 22 can provide an excitation signal at one or more discrete frequencies or sweep across one or more predefined frequency bands.

For example, during the first portion of a test phase, DS control 32 can control the transmitter 22 to provide the RF output signal within a first range of frequencies (e.g., a low frequency range). During a subsequent or other different phase of the sensing process, DS control 32 can control the transmitter 22 to provide the RF input signal for a different range of frequencies for exciting the DS sensor and the associated MUT disposed in the fluid channel 18. The receiver 24 thus can receive and provide corresponding RF output signals associated with each phase of the sensing process. As disclosed herein, the receiver 24 can be configured (e.g., analog and/or digital circuitry) to process the received input signal from each DS sensor, such as by performing amplification, filtering and down-conversion. DS control 32 can also control the receiver to provide the RF output data as a DC output voltage in the I mode and another DC output voltage in the Q mode.

The computing system 26 further can include data processing methods for computing permittivity in response to the RF output data provided by the receiver 24 during each part of the sensing process. Thus, the computing system 26 further can process the received input signals from a given sensor (or sensors) and provide output data that includes the results of the data processing representing complex permittivity as well as raw data corresponding to the RF output signal received by the receiver.

In some examples, the computing system 26 can also include a calibration process 36 programmed (e.g., see method 500 in FIG. 15) to calibrate the system interface system 14 and the DS sensor 16. For example, one or more reference MUTs (having a known permittivity) can be inserted into the fluid channel 18 and the DS control 32 can control the transmitter 22 to provide the excitation signal ($RF_{IN}$) to the DS sensor 16 over a corresponding range of frequencies, which can vary according to the reference MUT. For each MUT, the receiver 24 can measure the system output signal ($RF_{OUT}$) at each respective excitation frequency, which can include separate I and Q components. The calibration method 36 can further be programmed to fit the measured output signals for each reference MUT at given frequency to predetermined permittivity values predetermined for each respective reference solution. The functional relationship between system outputs at each excitation frequency can be stored in memory and utilized by data processing block 32 to convert the measured system output signal $RF_{OUT}$ at a given excitation frequency to a corresponding permittivity (e.g., complex permittivity) for an unknown MUT.

As an example, the functional relationship between measured system output signals $RF_{OUT}$ for each of the reference solutions at a given excitation frequency can be stored in memory as a look-up table programmed to provide an output of complex permittivity in response to the measured system output signal $RF_{OUT}$ and input excitation signal. There can be a given LUT for each frequency or the functional relationships between permittivity, excitation frequency and measured output can be stored in other forms of data structures or mathematical functions that can computed to calculate complex permittivity for a given MUT in response to the measured system output signal $RF_{OUT}$ and input excitation signal. Once the calibration method 36 has been programmed for a set of reference MUTs, the DS apparatus 10 is ready for measurement and determining complex permittivity for unknown MUTs. It is understood that the calibration of the system 10 can be implemented by a manufacturer of the system 10 or prior to conducting measurement by a user in the field.

The computing system 26 can provide the output data to a remote device 30 via a corresponding communication system 28. For example, the communication system 28 can include a communication interface configured to communicate data (e.g., via a corresponding communication link), demonstrated at 31. The communication link 31 can be implemented as a physical connection (e.g., an electrically conductive connection or optical fiber) or a wireless link (e.g., implemented according an 802.11x standard or other short range wireless communication).

The remote device 30 can be communicatively coupled to the DS apparatus 10 via the communication link. The remote device 30 can include a display 38 that can present the results from the data processing system. This can include graphs or other indications, (including graphics and/or texts) to provide the user results from the DS applied to the MUT within the fluid channel 18. The device 30 can be a general purpose computing device (e.g., notebook computer, laptop, desktop computer or the like) or it can be a special purpose device configured to interact with the DS apparatus 10 via the link 31.

The remote device 30 can also include a user interface 40. The user interface 40 can be utilized to program the DS apparatus 10 for one or more parts of a sensing process such as disclosed herein. For instance, the user interface 40 can be utilized to set the range of one or more frequencies, including one or more frequency bands, to be implemented as the excitation signal during testing of the MUT. For instance, in response to user input instructions entered at the remote device via the user interface 40, the computing system 26 can receive instructions via the link 31. The computing system 26 can in turn employ its control 32 to provide corresponding instructions to program the transmitter 22, which instructions can be stored in memory (e.g., a program register) of the transmitter to control the frequency of the excitation signal applied during a test process. Additionally or alternatively, the user interface 40 can be utilized to specify one or more MUTs that may have known characteristics such as for calibration of the DS apparatus 10. The user interface 40 can also be utilized to control the information that is presented in the display 38 as well as other post processing functions and data analysis.

In some examples, the sensing apparatus 12 can be configured to include two or more of substantially identical sensing structures, each including a respective DS sensor 16 disposed within a respective separate fluid channel 18. For instance, the transmitter can be controlled to provide excitation signals to each of the different DS sensors 16 having different frequency ranges. For example, if two DS sensors are utilized, the control 32 operates the transmitter 22 to provides a lower range of frequencies to excite one DS sensor during a portion of the measurement and a higher range of frequencies to excite the other DS sensor during another, different portion of the measurement. In this example, each DS sensor could be coupled to separate front end electronics configured to provide appropriate filtering and amplification according to the particular frequency ranges applied to excite each DS sensor. The data processing methods can aggregate the resulting RF output signal from the receiver 24 to calculate permittivity for each MUT for characterization.

As another example, where one or more pairs of DS sensors are utilized (e.g., example sensor of FIGS. 2-4), the MUT can be provided into the fluid channel 18 of one of the sensing structures and a known material (e.g., having a predetermined dielectric permittivity) can be provided into the fluid channel of another of the pair of sensing structures. In such an example, the sensor interface can provide a differential RF input signal (e.g., RF+ and RF−) to sensing electrodes of respective DS sensor circuits. Another sensing electrode of each of the DS sensor circuits can be coupled to a common node to provide the RF output signal to the sensor interface system 14. The RF output signal thus can have a predetermined mathematical relationship with the difference in dielectric permittivity for the fluid under test relative to the known fluid in the other fluid channel. The sensor interface system 14 thus can be configured to model this relationship and provide an OUTPUT indicative thereof the difference in dielectric permittivity for fluid under test.

Figure 2:
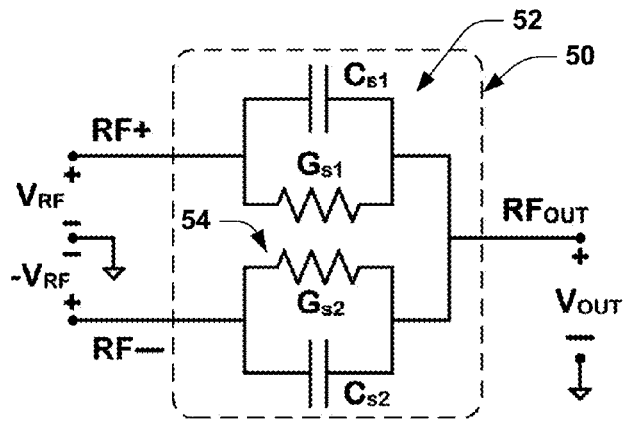
FIG. 2 depicts an example of a circuit model for a differential capacitive sensor of FIGS. 3 and 4.

FIG. 2 demonstrates an example of a sensing circuit 50 that could be employed to model the DS sensor circuitry 16 for the differential example disclosed herein. The sensing circuit 50 includes inputs RF+ and RF−, which are driven by differential input voltage $+V_{RF}$ and $-V_{RF}$ having an excitation frequency ($\omega$), such as supplied by transmitter 22. One DS sensor 52 is demonstrated as a capacitor $C_{S1}$ in parallel with a conductance $G_{S1}$. Another DS sensor 54 includes a capacitor $C_{S1}$ in parallel with a conductance $G_{S2}$. The capacitance and conductances can be related to the excitation frequency ω and the complex dielectric permittivity of the fluid as follows:

$$C_{S1} = C_0(\epsilon_r' + \Delta\epsilon_r')$$

$$G_{S1} = \omega C_0(\epsilon_r'' + \Delta\epsilon_r'')$$

$$C_{S2} = C_0\epsilon_r'$$

$$G_{S2} = \omega C_0\epsilon_r''$$

where the MUT in the channel (e.g., channel 18) has a complex dielectric permittivity of $\epsilon_r = \epsilon_r' - j\epsilon_r''$. Additionally, the capacitive sensing area admittance given the excitation frequency ω, can be expressed as follows:

$$Y_S = \omega C_0 \epsilon_r'' + j\omega C_0 \epsilon_r',$$

The output of the circuit 50 can thus be represented as follows:

$$V_{OUT} \propto V_{RF} \omega C_0 (\Delta\epsilon_r'' + j\Delta\epsilon_r')$$

where the sensor is driven by a differential RF/microwave signal ($\pm V_{RF}$) and loaded with a reference solution as well as an SUT with a small $\Delta\epsilon_r$.

Figure 3:
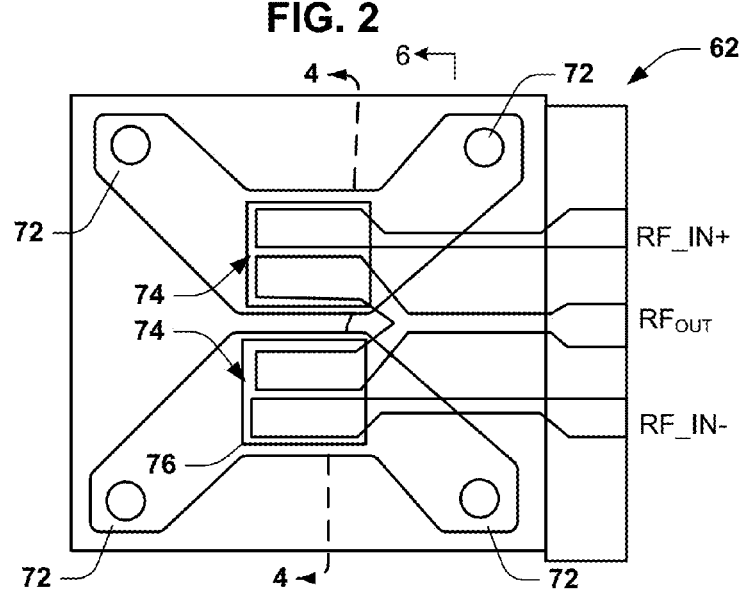
FIG. 3 depicts an example of a differential dielectric spectroscopy sensor.
Figure 4:
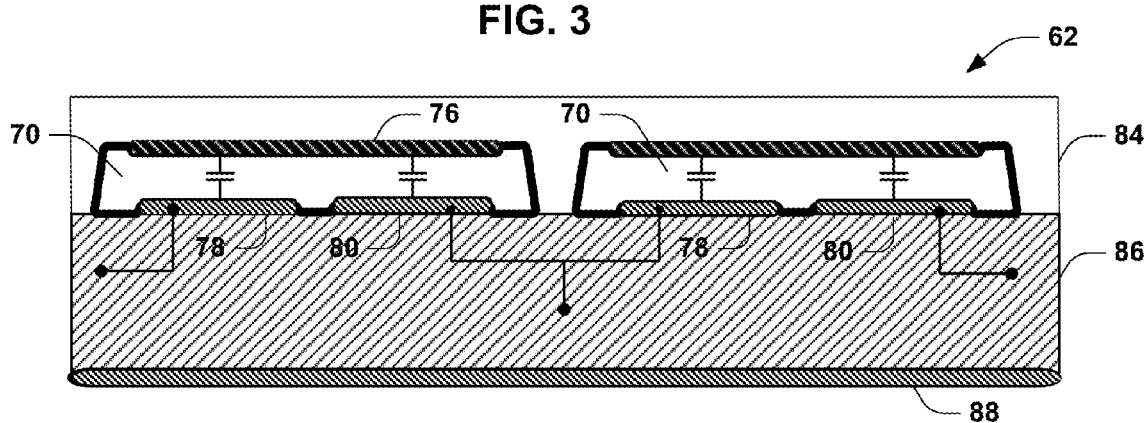
FIG. 4 depicts a cross sectional view of the sensor of FIG. 3.

FIGS. 3 and 4 depict an example of a three-dimensional sensing DS sensing apparatus 62. The sensing apparatus 62 can be electrically coupled to a sensor interface system (e.g., interface 14), such as via contact pins. Other types of connections (e.g., electrically conductive or wireless) could also be utilized to provide for bi-directional communication with respect to the DS sensing apparatus 62.

In the example of FIGS. 3 and 4, the interface system (e.g., transmitter 22) provides differential RF input signals to differential inputs RF+ and RF− of the DS sensing apparatus 62. The DS sensing apparatus 62 includes circuitry having a complex admittance that varies as a function of dielectric permittivity of fluid within respective fluid channels, such as disclosed herein. The DS sensing apparatus 62 provides an output signal to the interface system via an output connection $RF_{OUT}$ (e.g., a pin or other type of connection).

In the example of FIGS. 3 and 4, the sensing apparatus 62 includes a pair of fluid channels 70 into which a volume of fluid (e.g., liquid or gas) can be introduced via ports 72 (e.g., inlet and outlet holes). Capacitive sensors 74 are disposed within each fluid channel. Each capacitive sensor 74 includes a floating electrode 76 spaced apart from and opposing sensor electrodes 78 and 80 to provide respective sensing areas (e.g., corresponding to the area of overlap between the floating electrode and associated sensor electrodes). The sensor electrodes 78 and 80 in each capacitive sensor 74 can be electrically isolated from each other. The RF+ input signal is coupled to a sensor electrode of one of the capacitive sensors. The RF− input signal is coupled to a sensor electrode of another of the capacitive sensors. The other sensor electrodes of each of the capacitive sensors are coupled to a common node electrically coupled to provide $RF_{OUT}$.

As demonstrated in the cross-sectional view of FIG. 4, the each sensor 74 includes planar sensor electrodes are separated from a floating electrode through a microfluidic channel to form a capacitive sensing area with nominal air-gap capacitance, $C_0$, defined by the electrode area and microfluidic channel height. As mentioned above, at the excitation frequency ω, the capacitive sensing area admittance is $Y_S = \omega C_0 \epsilon_r'' + j\omega C_0 \epsilon_r'$, when the channel is loaded with an MUT having a complex dielectric permittivity of $\epsilon_r = \epsilon_r' - j\epsilon_r''$. In the example of FIGS. 3 and 4, two identical sensing structures 74 are be electrically connected by a common output node, $RF_{OUT}$, to form a differential sensor, where $V_{OUT} \propto V_{RF} \omega C_0 (\Delta\epsilon_r'' + j\Delta\epsilon_r')$ when the sensor is driven by a differential RF/microwave signal ($\pm V_{RF}$) and each separate structure is loaded with a reference solution or an MUT with a small $\Delta\epsilon_r$.

The differential measurement can help enhance the sensing resolution, because the interface IC would not need to measure a very large voltage proportional to the nominal permittivity, $\epsilon_r$, as may otherwise be the case with a single-ended sensor. The exact relationship between $V_{OUT}$ and $\Delta\epsilon_r$ depends on the complex impedance (admittance) seen at the output node $RF_{OUT}$, which includes the IC input impedance and the parasitic impedance of interconnect. As disclosed herein, the sensor 62 and associated parasitic impedances can be modeled, and in-circuit calibration can be performed employing known reference materials to model the relationship between $V_{OUT}$ and $\Delta\epsilon_r$ for use in identifying the permittivity of the fluid under test and, in turn, characterizing and identifying the fluid. If the parasitic impedance of the contact pins proves to have a significant effect on sensor operation, a reliable electrical connection through direct wire-bonding of the sensor and IC can be implemented at the expense of sensor replacement time. Another approach to deal with parasitic impedance is through calibration by increasing the number of reference solutions at the expense of calibration complexity.

As also demonstrated in the cross sectional view of FIG. 4, the sensor can be fabricated in multiple parts that are attached together to provide a resultant monolithic sensor structure 62. For example, the sensor 62 can include a top part 84 and a bottom part 86. The bottom part 86 includes sensor electrodes 78 and 80 and RF signal routing (e.g., traces) fabricated on a substrate, which can also include a ground plane 88 for the sensor 62. The top part 84 can be fabricated separately from the bottom part 86. The top part 84 can include the fluid channel 70 for each sensor structure 74, such as a recess formed in a wall of an insulating substrate material. The top part 84 can also include inlet/outlet ports 72 to provide fluid communication for accessing the volume defined by the channel 70. For example, the channel 70 and associated ports 72 can be fabricated by micromachining (e.g., laser micromachining) or by other types of machining or etching techniques. In some examples, the surface of channel 70 further can be coated with a polymer or other material (e.g., electrically insulating film, such as poly(ethylene glycol)) to help protect against protein adsorption onto the surfaces that contact the protein solutions. The polymer can be applied via physisorption or chemisorptions, for example.

As one example, the bottom part 86 can be fabricated using standard techniques with a 4" borosilicate glass wafer as the substrate. A 100-Å/1,000-Å Cr/Au layer can be evaporated on both sides of the wafer. The top metallization can further be patterned with lift-off to create the sensor electrodes 78 and 80, microstrip signal lines and contact pads. A further bottom metallization can be employed to serve as a ground plane for the sensor 62.

As a further example, the microfluidic cap will be fabricated using poly(methyl methacrylate) (PMMA). The channel height (e.g., distance between top and bottom surfaces of each channel 70) can be established according to application requirements for the sensor. For instance, a channel height of about 50 μm can be implemented for potential use with human blood cells. The floating electrodes can be deposited on the inner top surface of the microfluidic channels by evaporating a 1,000-Å Au layer and patterning with lift-off.

In the example of FIG. 3, the sensor 62 is demonstrated along with its terminals that can be electrically connected to interface electronics on a printed-circuit board (PCB). In some examples, the connection between the sensor apparatus 62 and interface system 14 can be configured as a plug-and-play-type connection between the sensor contact pads and PCB input/output pads (e.g., using spring-loaded contact pins to provide an electrical connection). The connection method facilitates DS measurements with potentially hazardous or contaminating solutions, since the low-cost sensor can be replaced after a measurement without contaminating the entire instrument. That is, in some examples, the sensor 62 can be for single use, which can be discarded and replaced after each use, while the interface system 64 and associated electronics can be re-useable. In other examples, the sensor can be repeatedly reused for a plurality of measurements with the same or different fluids under test. The interface system 64 can be calibrated to facilitate measuring the dielectric permittivity for a given type of one or more fluids.

As an example, sensor calibration can be performed by loading the sensor differentially with DI water as a reference solution and a mixture of DI water and one of several organic solvents (e.g., methanol, isopropyl alcohol (IPA)) at various concentrations to produce an SUT with a small $\Delta\epsilon_r$ from that of DI water. The transmission characteristics of the sensor can be measured with a VNA over a range of frequencies (e.g., from 5 MHz to 10 GHz), and a calibration algorithm can be derived based on such measurements to relate the complex voltage transmission measurements to $\Delta\epsilon_r$. Sensor characterization can be performed in similar fashion with DI water and a mixture of DI water and ethanol as reference solution and SUT, respectively, and the extracted permittivity for the mixture will be compared to that from bulk-solution measurements using a commercial dielectric probe.

Figure 5:
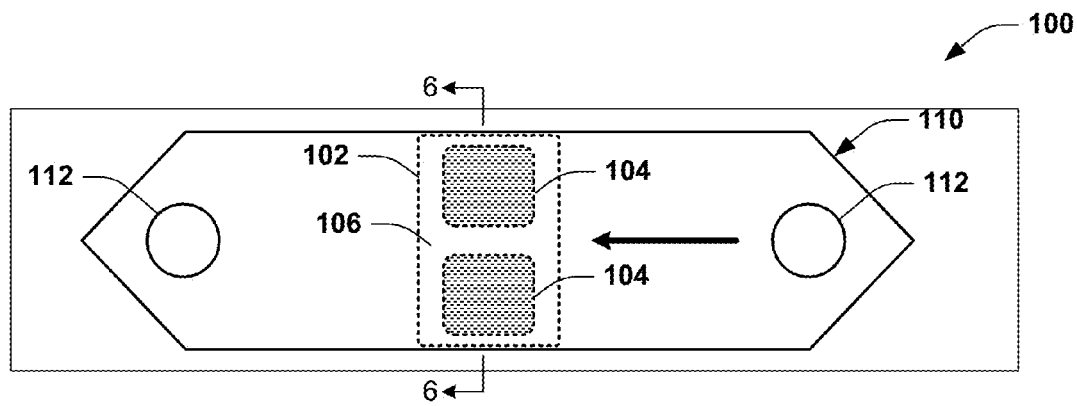
FIG. 5 depicts another example of a dielectric spectroscopy sensor.
Figure 6:
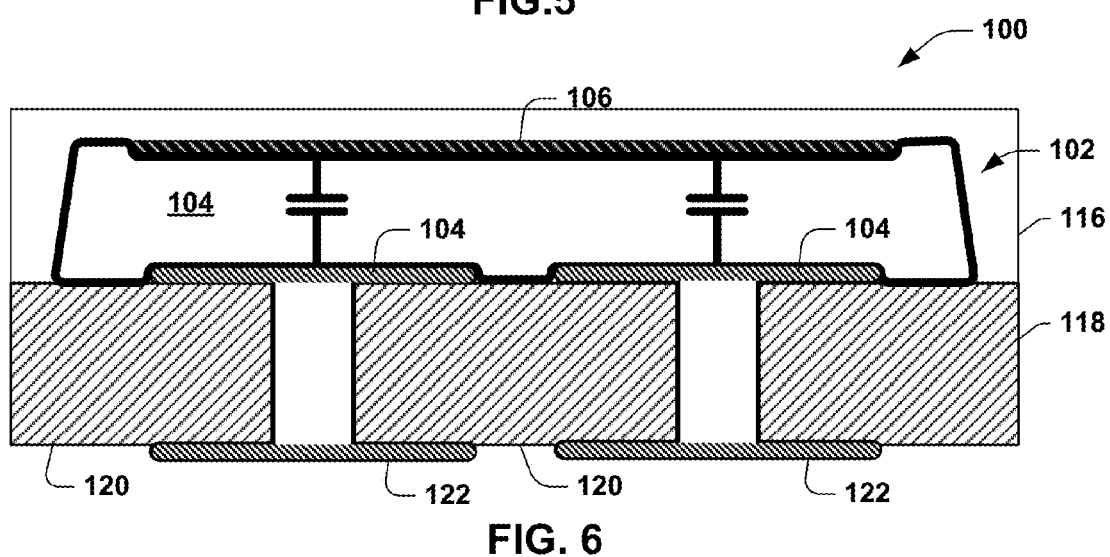
FIG. 6 depicts a cross sectional view of the sensor of FIG. 5 taken along line 6-6.

FIGS. 5 and 6 demonstrate an example of another sensing apparatus 100 (e.g., corresponding to apparatus 12) that can be utilized in the DS system 10. The apparatus 100 includes a three-dimensional, parallel-plate, capacitive sensing structure 102. The capacitive sensing structure 102 includes two planar sensing electrodes 104 that are spaced apart and are separated from a floating electrode 106 through a microfluidic channel 108 to form a 3D capacitive sensing area disposed within the microfluidic channel. The capacitive sensing structure 102 is disposed within a substrate material 110. The sensing apparatus 100 includes ports 112 (e.g., inlet and outlet holes) through which a volume of fluid (e.g., liquid or gas) can be introduced.

As also demonstrated in the cross sectional view of FIG. 6, the sensing apparatus 100 can include a top portion 116 and a bottom portion 118 (where bottom and top are relative terms simply to provide a frame of reference in the figure). The bottom portion 116 can include sensor electrodes 104. The electrodes can be electrically connected via electrically conductive sidewalls of respective vias 120. The electrically conductive vias thus can provide a path for RF signal routing between the respective electrodes 104 and associated electrical contact pads 122 fabricated on the substrate 118. In some examples, the top part 116 may be fabricated separately from the bottom part 86. The top part 116 can include the fluid channel 108 between ports 112 and extending between the floating electrode 106 and the sensing electrodes 104.

In some examples, a thin film or other surface coating (e.g., having a thickness that is smaller than the microfluidic channel height) can be applied to prevent direct contact between the MUT and the metal electrodes with minimal impact on sensitivity. As the MUT passes through the capacitive sensing area, the impedance (and hence admittance) of the sensor changes based on the dielectric permittivity of the MUT disposed in the channel 108.

Figure 7:
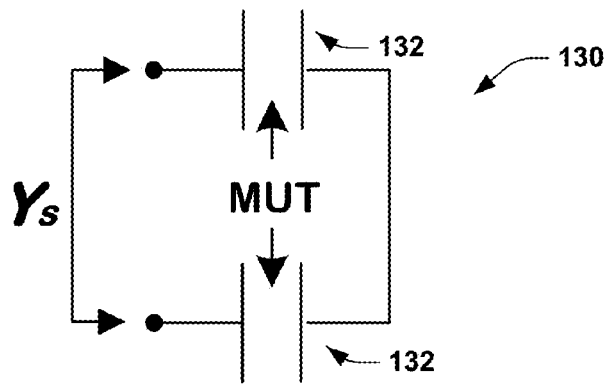
FIG. 7 depicts an example of a circuit model for the capacitive sensor of FIGS. 5 and 6.

FIG. 7 depicts an example of a circuit model 130 for the sensor of FIGS. 5 and 6. The circuit 130 model includes two series connected capacitors 132 (e.g., capacitors formed between floating electrode 106 and sensing electrodes 104 of FIGS. 5 and 6).

By way of example, at the measurement frequency, w, the admittance of the capacitive sensing area can be expressed as follows:

$$Y_S = j\omega C_0(\epsilon_r' - j\epsilon_r'')$$

which further can be represented by its real and imaginary parts of sensor admittance as follows:

$$\mathrm{Imag}\left(\frac{Y_s}{\omega}\right) = C_0 \times \epsilon_r' \text{ and } \mathrm{Real}\left(\frac{Y_s}{\omega}\right) = C_0 \times \epsilon_r'',$$

respectively, where C0 is the nominal, series-connected, air-gap capacitance of the parallel-plate, capacitive sensing area, and $\epsilon_r'$ and $\epsilon_r''$ are the real and imaginary parts of the complex relative permittivity of the MUT, respectively.

Figure 15:
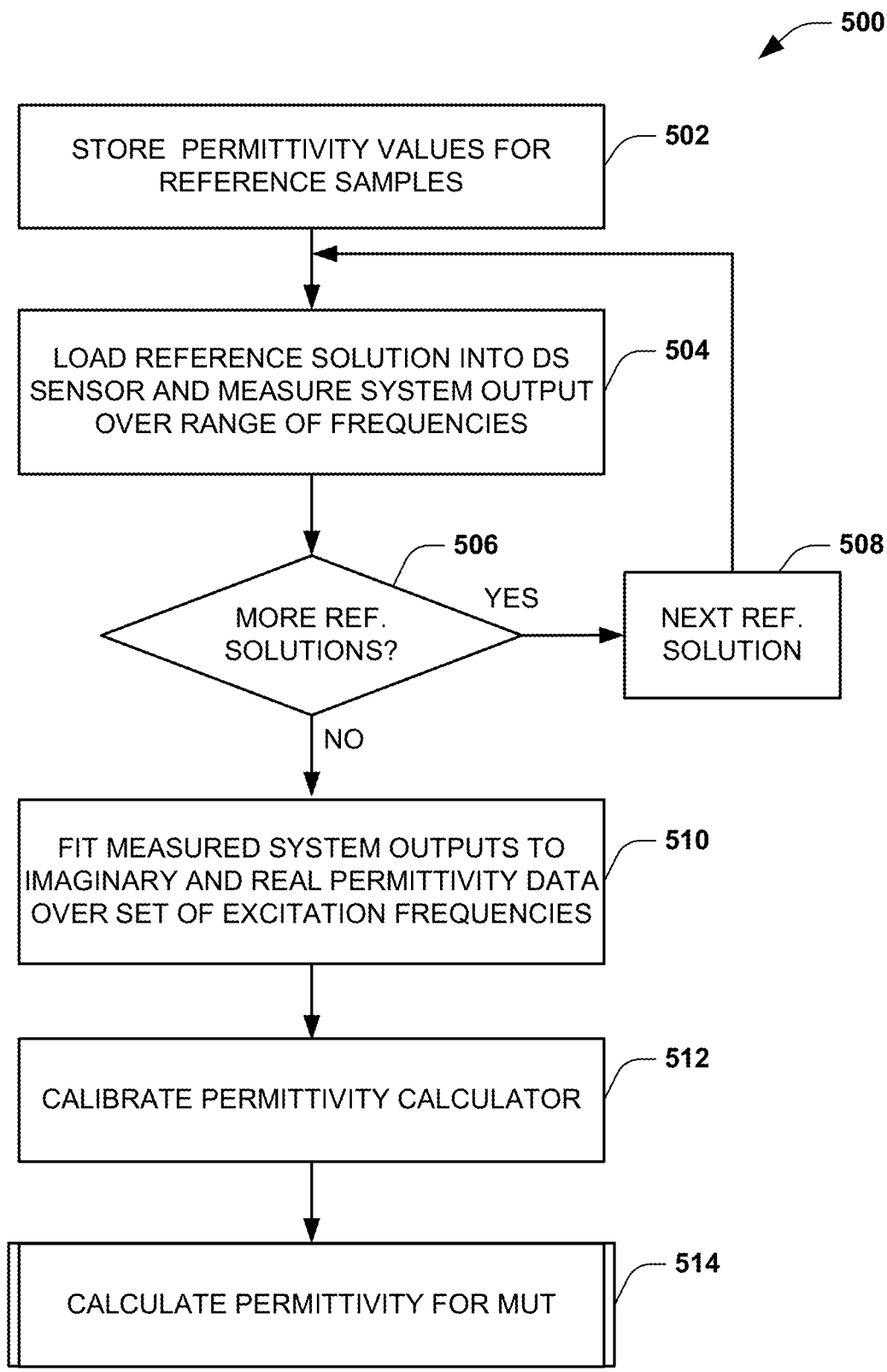
FIG. 15 is a flow diagram demonstrating an example method to calibrate and use a DS system.

In practice, parasitic inductance and parasitic capacitance from the vias 120 and contact pads 122 can be accounted for by implementing a calibration method, such as disclosed herein (see, e.g., calibration method 500 of FIG. 15).

Applying the sensing apparatus 100 in the context of the DS system 10, an input RF signal (e.g., sweeping over one or more frequency ranges) can be applied (e.g., by transmitter 22) to an input electrode 122 for exciting the sensing circuit. A resulting RF output signal can be measured at the other sensing electrode 122 (e.g., by receiver 24). The measured signal can be filtered and amplified (e.g., by analog and/or digital circuitry of receiver 24) and processed (e.g., by data processing 34 of computing system 26) to calculate permittivity for the MUT that resides within the channel 108. As disclosed herein, the data processing can be implemented to accurately measure both real and imaginary parts of the complex relative permittivity over a broad range of frequencies.

Figure 8:
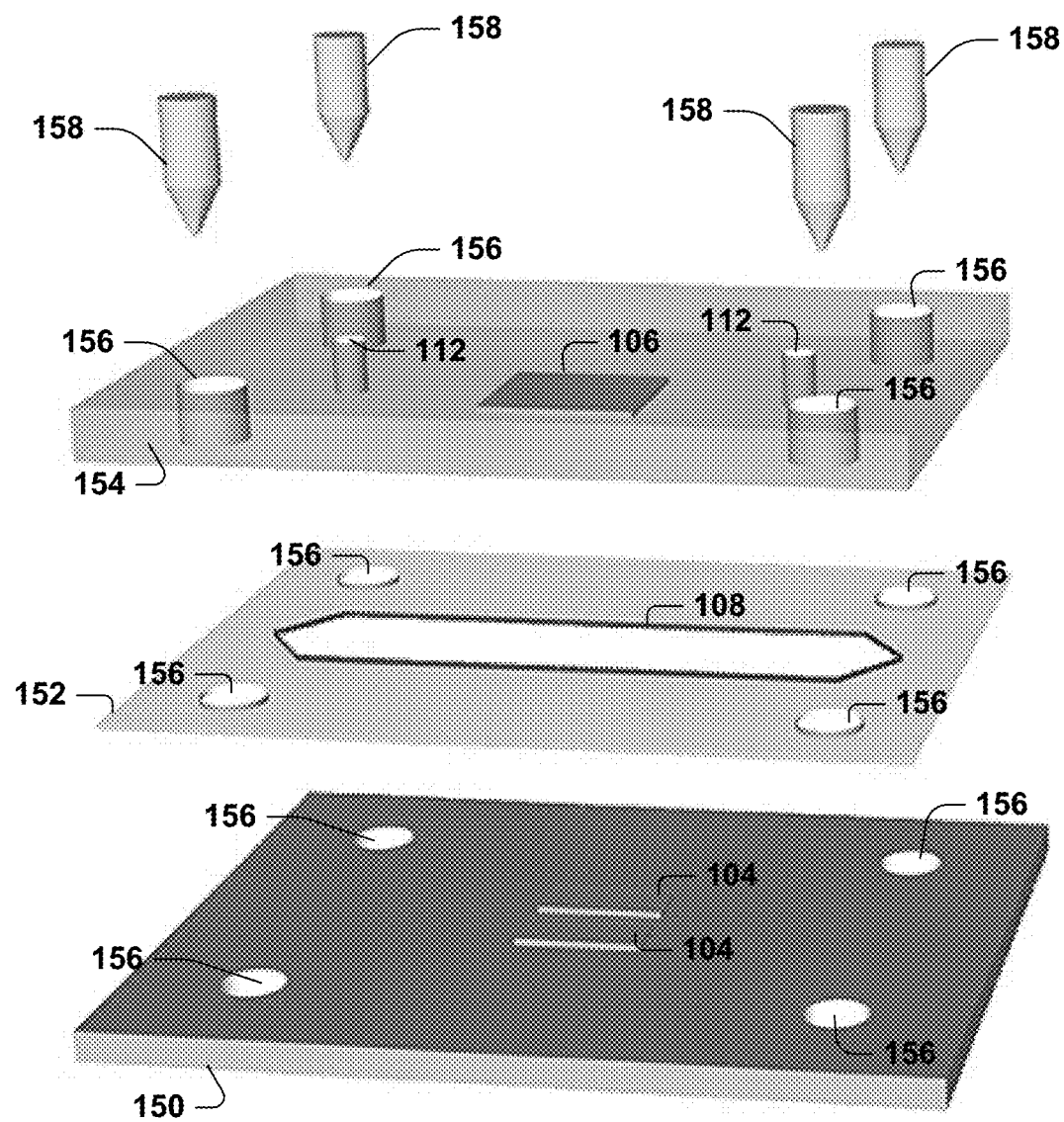
FIG. 8 is an assembly view showing part of an example fabrication process for making a sensor.

FIG. 8 illustrates an example of the sensor fabrication and assembly that can be employed to produce the sensing apparatus 100 of FIGS. 5 and 6. As an example, the sensing apparatus 100 can be constructed as laminated device that includes three layers, namely a connector layer 150, a channel layer 152 and a fluidic layer 154. The connector layer 150 can be fabricated from a substrate material (e.g., commercially available, 0.5 mm-thick, Rogers 4350 PCB). Sensing electrodes 104 can be formed (e.g., using the top PCB metal layer) on the adjacent surface of the connector layer. As one example, the electrodes 104 may be implemented to have dimensions of about 0.6 mm×0.6 mm with spacing of 0.4 mm. Electrical connections to the sensing electrodes 104 are made through vias in the substrate (e.g., PCB) of the connector layer 150, which can be electrically connected to the sensor interface system (e.g., to transmitter 22 and receiver 24 of interface 14) by connectors attached to the pads on the bottom side of the substrate layer 150 (not shown).

The channel layer 152 includes the microfluidic channel 108 formed therein. For instance, the channel can be laser-cut into a non-conductive material layer that is interposed between the layers 150 and 154. The layer 152 can be a thin film layer of double-sided-adhesive (DSA) material having a thickness that is much less than the electrode-containing layers 150 and 154. As one example, the layer 152 is about 250 µm thick, whereas the layer 150 is about 0.5 mm thick and layer 154 is about 3.2 mm thick. Other relative thicknesses can be utilized according to application requirements.

The fluidic layer 154 can be formed from a layer an electrically non-conductive material, such as a layer of an acrylic (e.g., PMMA acrylic) material. For instance, the fluid ports 112 can be formed (e.g., by laser micromachining) through the side surfaces of the cap layer as to overly spaced apart end portions of the channel 108. The floating electrode 106 can be formed by deposition of electrically conductive material deposited at a desired location (e.g., aligned with the sensing electrodes and within the channel 108) on the bottom surface that faces the surface of the layer 150 where the sensing electrodes are formed. For instance, the floating electrode 106 can be an electrically conductive material (e.g., gold, copper or aluminum) deposited on the inner top surface of the cap by sputter deposition using a shadow mask and lift-off process. As an example, the floating electrode can be formed with a thickness of 1000 angstroms and dimensions of 1.2 mm×2.8 mm aligned with sensing electrodes having dimensions of 0.6 mm×0.6 mm, each.

To facilitate construction of the sensing apparatus 100, each of the layers 150, 152 and 154 can include a plurality of alignment holes 156. Each of the layers can be connected together and held in place by inserting corresponding alignment pins 158 can be inserted into the holes 156. In some examples, a thin film coating of a barrier material (e.g., 1.5 µm layer of Parylene-N film or other polymer film) can be deposited on the surfaces of the layers 150 and 154 to protect the metal and plastic surfaces from direct contact with the MUT.

Microfluidic inlet/outlet holes 112 in the cap layer can be configured with a diameter to fit a standard micropipette tip. As one example, the microfluidic channel has a total sample volume of 9 µL and a volume of 0.8 µL in the sensing area under the floating electrode. Other volumes for the channel and sensing area can be implemented according to application requirements. The sensor 100 can be assembled by attaching the cap to the surface of the PCB substrate using the DSA film interposed therebetween. As mentioned, the alignment holes 156 and pins 158 can be used to align the microfluidic channel and floating electrode over the sensing electrodes.

Figure 9:
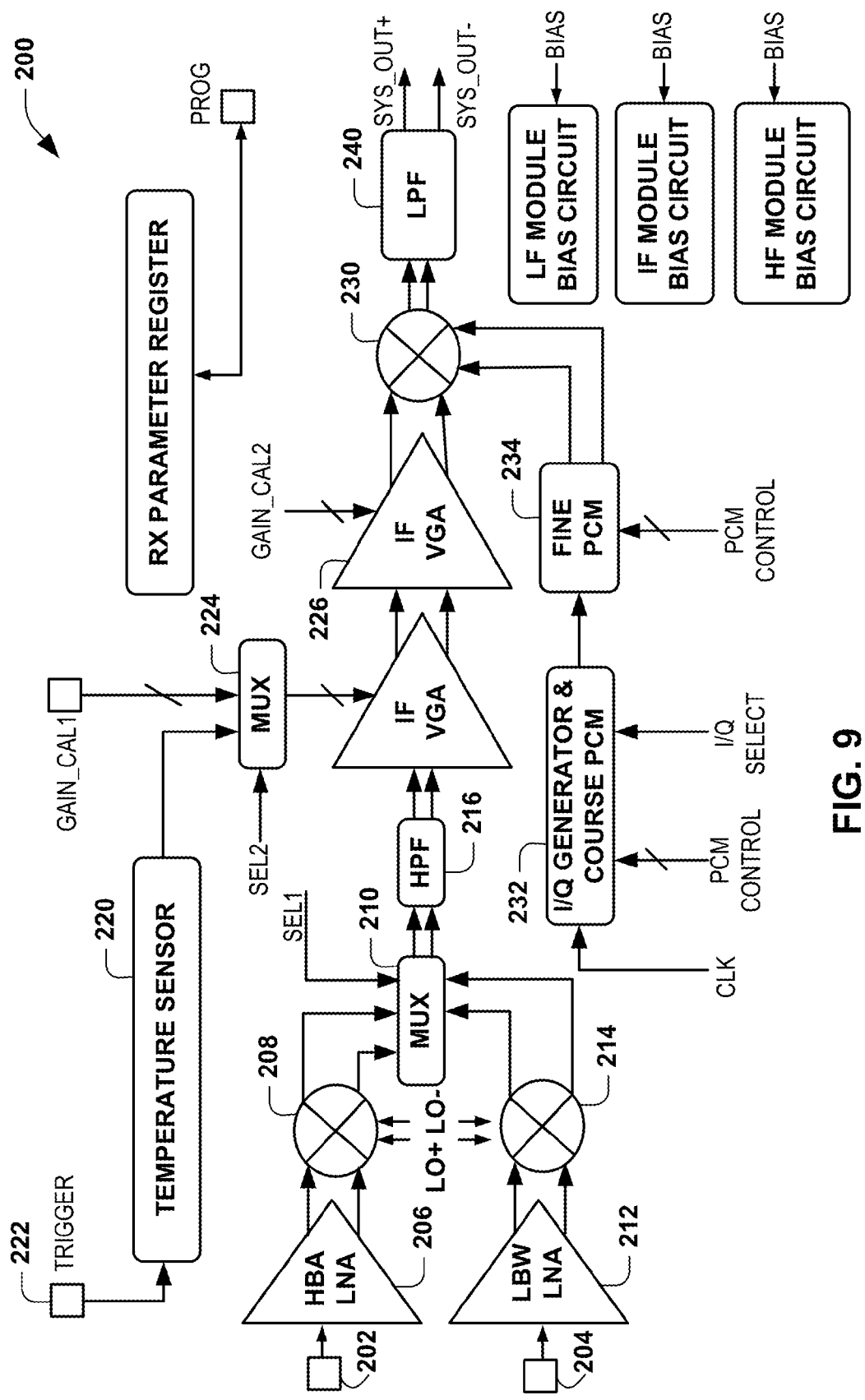
FIG. 9 depicts an example of receiver circuitry that can be implemented in a sensor interface system.

FIG. 9 depicts an example of a receiver circuit 200, which can be implemented as receiver 24 in FIG. 1. The receiver circuit 200 is configured to measure transmission characteristics of the DS sensor (e.g., sensor 16) in voltage domain based on an output $V_{OUT}$ from the sensor. While in the example of FIG. 9, the receiver 200 provides an analog output at system outputs (System$_{OUT}$+ and System$_{OUT}$-), in some examples, the receiver can include an analog-to-digital converter (ADC) to provide a digital output for further processing corresponding to System$_{OUT}$+ and System$_{OUT}$-. Additionally, the design of the RX 200 can include an optimized architecture to extend the operation frequency to 10 GHz or greater.

The receiver 200 includes one or more inputs 202 and 204 to receive input signals from the sensor responsive to signals provided by a transmitter (e.g., transmitter 22) to excite the sensor, as disclosed herein. In some examples, a single input 202 or 204 may suffice for measuring transmission characteristics. In other examples, such as where a more broadband range of frequencies are applied to the sensor, more than one input 202-204 can be used.

In the example of FIG. 9, the receiver 200 includes a pair of inputs 202 and 204, demonstrated respectively at HF_RFin and LF_RFin, where each input is used for measuring a different range of frequencies. Thus, each input 202 and 204 is connected to drive associated front end circuits configured to perform front-end processing (e.g., filtering, amplification and mixing) for a predefined range of frequencies (e.g., about 200 MHz to about 5 GHz). For instance, the input HF_RFin is provided at 202 to a high bandwidth (HBW) path that includes a HBW low-noise amplifier 206. The HBW LNA 206 can perform single to differential conversion and provide an amplified differential output to an HBW mixer 208. The mixer 208 (e.g., a Gilbert-cell active mixer) can down convert the amplified signals from the amplifier 206 based on local oscillator input signals LO+ and LO− to provide IF signals (e.g., concerting input frequency in the range of MHz to GHz down to IF of about 1 MHz). The signals LO+ and LO− can be provided by transmitter circuitry (see FIG. 10). The IF differential signals can be provided to a multiplexer 210.

Similarly, the input LF_RFin is provided at 204 to a low bandwidth (LBW) path that includes a LBW LNA 212. The LBW LNA 212 is configured to perform single to differential conversion and provide an amplified differential output to an LBW mixer 214 based on frequency down conversion according to local oscillator input signals LO+ and LO. The frequency-converted, LBW differential signals can be provided to the multiplexer 210. The multiplexer can be operated to pass either the pre-processed HBW or LBW signals to a high-pass filter 216 depending on the frequency range of the excitation signals, which can be set as programmable control signals (e.g., from control 32 of computing system 26).

By way of example, an external bit (or other control input, such as provided by control 32) can be set to control a multiplexer 210 to route the appropriate front end module output to the input of a coherent detector for a second down-conversion step. Since, in some implementations, each of the front end RF modules will have independent power supplies, they can be turned on and off independently. This feature allows the user to save power by using the LBW RF module only, in case the experiment does not require GHz-range excitation frequencies, for example. Additional controls can be provided to set bias currents for the different front end modules.

The receiver 200 further can implement amplification of the IF signal from the filter with gain and temperature calibration. For example, the highpass filter 216 can provide a filtered output signal to differential inputs of an intermediate frequency (IF) variable gain amplifier stage 218 that is configured to provide temperature compensation. A temperature sensor 220 can be activated in response to a trigger input at 222 to provide a temperature compensated gain value to a multiplexer 224. For example, the gain of the first VGA can be adjusted by a digital output of the on-chip temperature sensor 220 to compensate for gain decrease versus temperature in a defined temperature range (e.g., 0 to 60° C.).

The multiplexer 224 can switch between the temperature signal and another gain calibration input to calibrate the IF VGA 218. The IF VGA 218 can provide the temperature compensated amplified IF output to another IF VGA 226 for additional amplification according to a gain calibration (Gain_Cal2), which can be fixed or variable. The IF VGA 226 provides its amplified output to a passive mixer 230. Each of IF VGAs can be operated in response to bias control currents supplied to the receiver 200.

The amplified/filtered IF signal can be down-converted to DC via a passive mixer 230 and low pass filter 240. For example, a clock drives a digital I/Q generator with a clock signal (e.g., 1-MHz) and then phase-adjusted using a phase calibration module (PCM). The PCM can provide square-wave, I/Q signals to the passive mixer 230. Given the path delay experienced by sensor response signal at each excitation frequency, the fine PCM 234 can refine delay to I/Q signals (same delay to preserve the 90° phase shift) before they drive the passive mixer 230. The I/Q signals output of the passive mixer 230 can be low pass filtered and provide the output signal System$_{OUT}$+ and System$_{OUT}$−. For instance, output signal System$_{OUT}$+ and System$_{OUT}$− can be provided to an ADC for generating a corresponding digital output signal for further processing (e.g., by data processing methods 34).

The LNAs 206 and 212 and, mixers 208 and 214 thus provide a broadband lock-in architecture, to down-convert the sensor response signal at the RF/microwave excitation frequency to an IF frequency. The next stages and passive mixing provide additional down-conversion to dc using a coherent detector to extract the dc component of the system output. The dc component would be proportional to the imaginary (real) part of sensor $V_{OUT}$ in I(Q) mode of system operation. While the example of FIG. 9 shows two different bandwidth paths, fewer or greater numbers of paths could be utilized in other examples to accommodate different frequency ranges.

Figure 10:
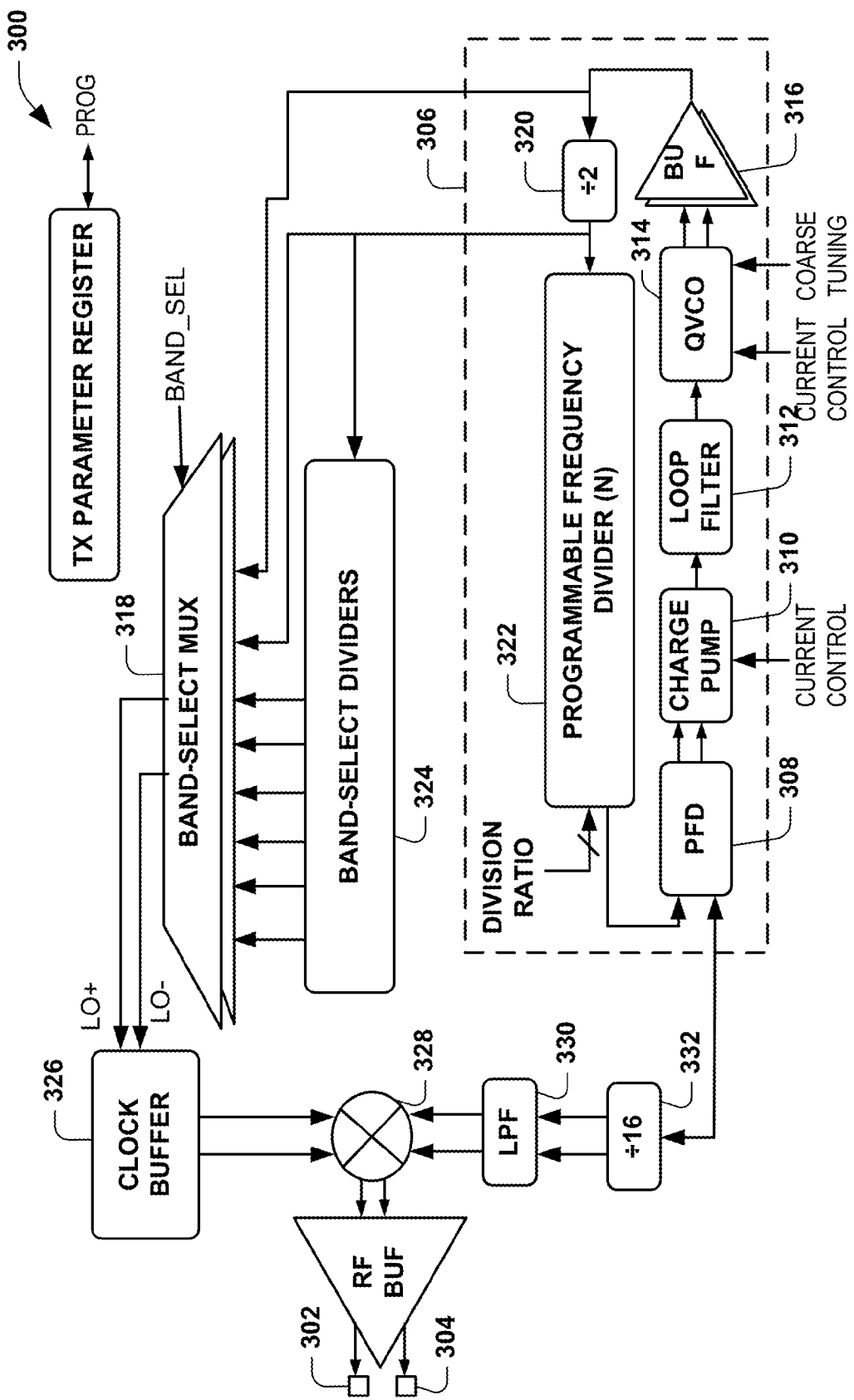
FIG. 10 depicts an example of transmitter circuitry that can be implemented in a sensor interface system.

FIG. 10 depicts and example of a transmitter circuit 300 such as corresponding to the transmitter 22 of FIG. 1. The transmitter 300 is configured to generate differential RF excitation signals, demonstrated as RF_OUT+ and RF_OUT−, for exciting a sensor (e.g., sensor 16) connected at outputs 302 and 304. The transmitter 300 can also generate local oscillation signals (LO+ and LO−) for use in down-converting signals by the receiver circuitry 200. As an example, the operation frequency can range from about 1 MHz to about 10 GHz, such as can be controlled in response to control inputs from an associated computing system (e.g., control 32 of computing system 26). For example, transmitter 300 can provide the excitation signal in a range defined by one of a plurality of predefined frequency bands. For example, the transmitter 300 can be set to one or more desired pre-selected specific frequency points in response to a band select signal (e.g., set in response to control signal from control 32). Alternatively, the frequency synthesizer can be configured to sweep the excitation frequency over one or more specific ranges in response to the band select signal (e.g., set in response to control signal from control 32).

By way of further example, the transmitter 300 includes an integer-N frequency synthesizer 306 operating in a predefined range (e.g., from about 1 MHz to about 10 GHz) to provide the RF output signal at 302 and 304. The frequency synthesizer 306, for example, includes a phase-frequency detector (PFD) 308, current-programmable charge pump 310, loop filter 312, quadrature VCO (QVCO) 314. The QVCO can include both coarse and fine tuning. The frequency synthesizer 306 can also include a buffer 316 that provides a buffered output to an input of a band select multiplexer 318 as well as to a divider (e.g., a ÷2 divider) 320. The output of divider 320 can drive a programmable frequency divider 322 with a ratio (N) in a predetermined range according to the value of the programmable input (e.g., ranging from 150 to 320). The output of divider 320 can also provide another frequency band input to the multiplexer 318 as well as drive band select dividers 324. The band select dividers 324 can include an arrangement of band-select, frequency divide-by-2 blocks (see, e.g., FIG. 12) configured to generate lower excitation frequencies (e.g., from about 1 MHz to about 5 GHz. The output of the multiplexer 318 is selected based on a band select control signal to provide local oscillator signal (e.g., a differential signal LO+ and LO−) to a clock buffer 326. The multiplexer 318 thus can route the generated differential LO signal to both the RX circuitry (receiver 200) and a clock buffer 326.

The transmitter 300 further can include a mixer 328 configured to generate the excitation signal for the sensor 106 by mixing the LO+ and LO− signal (from clock buffer 326) with a predetermined low frequency signal (e.g., 1-MHz signal). For example, the input clock signal (e.g., a 16-MHz reference clock) can be provided to a frequency divider 332 (e.g., a divide-by-16 divider) and filtered by low-pass filter 330 to provide a filtered RF signal at a desired frequency that is supplied to the mixer 328. The mixer 328, for example, is a harmonic-rejection, single-sideband (HR-SSB) mixer, which can reject the up-converted as well as $3^{rd}/5^{th}$ harmonic mixing terms at its output, resulting in a nearly single-tone excitation signal at 302 and 304 for the sensor. Further, the mixer 328 can inherently have a differential output to allow driving a differential sensor, if desired. Additionally, the mixer can employ a programmable conversion gain for tunability in the excitation amplitude ($\pm V_{RF}$) to ensure that $V_{OUT}$ can lie within the input dynamic range of the IC for a desired range of $\Delta \in_r$.

As a further example, the synthesizer 306 can be configured to have a constant loop gain K ($\propto K_{VCO} \times I_{cp}/N$), such as by keeping a constant VCO gain factor ($K_{VCO}$) and varying the charge pump current ($I_{CP}$) in proportion to the programmable frequency-divide ratio (N). This can help ensure stability and constant settling time for the synthesizer within the entire frequency range of operation.

Figure 11:
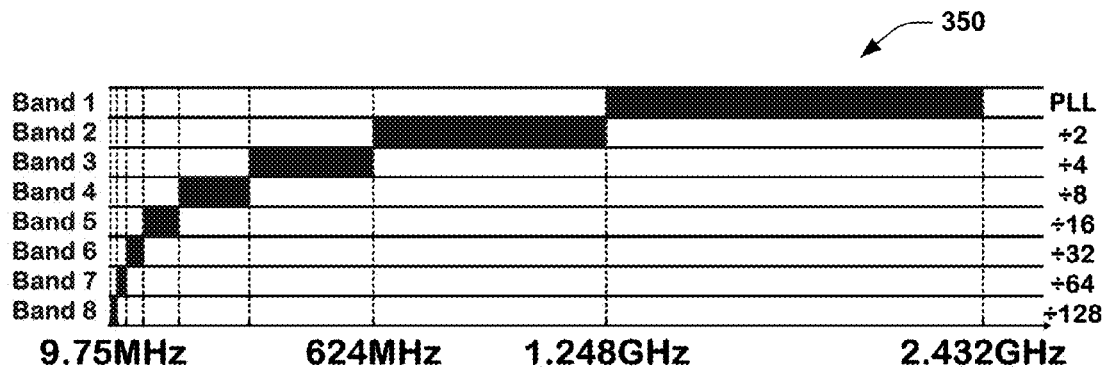
FIG. 11 is a graph demonstrating frequency bands that can be provided by the transmitter circuitry of FIG. 10.

FIG. 11 is a graph 350 demonstrating a plurality of frequency bands that can be provided by the transmitter 300 of FIG. 10. In the example of FIG. 11, eight discrete bands in a continuous range from 9.75 MHz to 2.432 GHz are depicted. Each band can be generated to provide respective I and Q components for each band.

Figure 12:
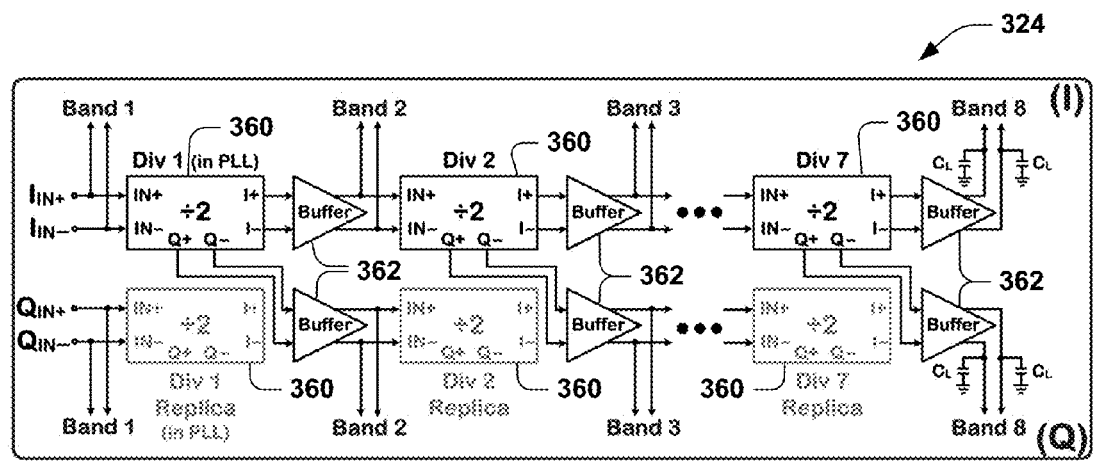
FIG. 12 depicts an example of band select divider circuitry that can be utilized to select frequency bands for exciting a DS sensor.

As a further example, FIG. 12 depicts an example the band select divider circuitry 324 that can provide each of the bands, such as the bands shown in FIG. 10. The band select divider circuitry 324 can include an arrangement of band-select, frequency divide-by-2 blocks 360 configured to supply respective differential frequency outputs of two for each of the I and Q components. The differential I and Q outputs are provided to buffers for each band. Each buffer 362 supplies its differential signal at a prescribed frequency to inputs of the multiplexer 318, which selects a respective band, including its I and Q components, based on the band select input.

Figure 13:
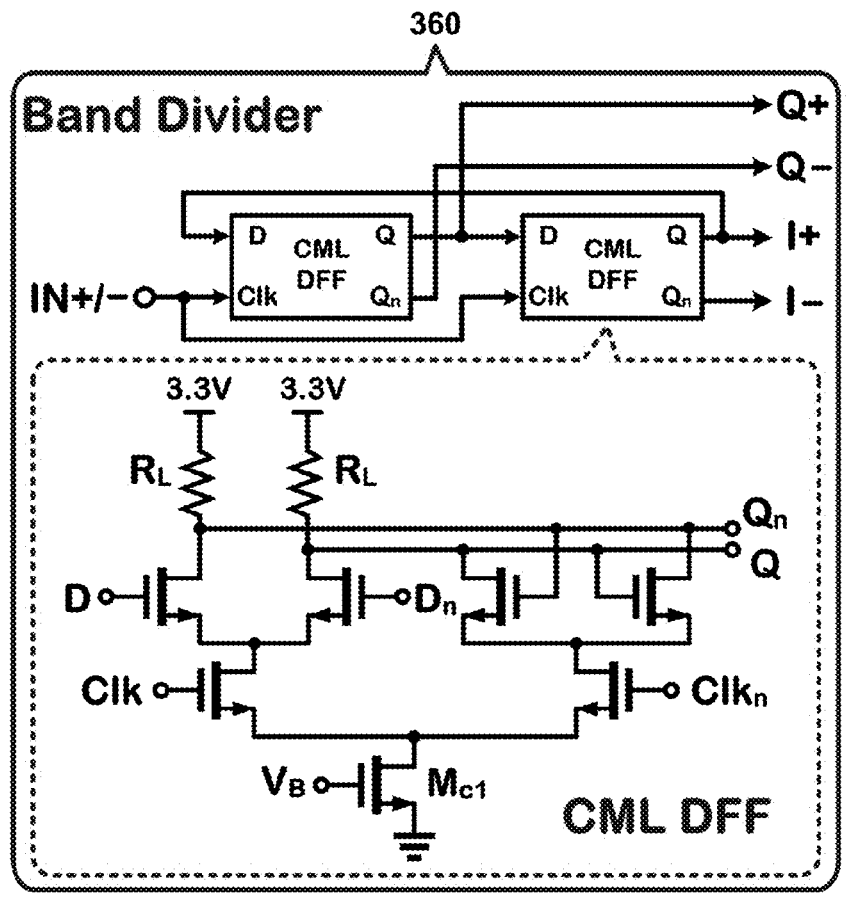
FIG. 13 depicts an example of frequency divider circuitry that can be utilized in the transmitter circuitry of FIG. 10.

FIG. 13 depicts band divider 360 that can be implemented in the band select divider circuitry 324 to divide the generated frequency signal into respective frequency bands for use within the transmitter circuitry of FIG. 10. In the example of FIG. 13, the band divider 360 is demonstrated as divide-by-two circuit of a pair of D-flip flops connected in series; although other approaches (e.g., analog or digital circuitry) can be used to implement frequency dividers for the respective bands. One of the flip-flops provides the differential Q components for a respective frequency band and the other flip-flop provides the differential I components for the respective frequency band. Any number of such band dividers can be connected together to accommodate any number of bands with a desired frequency range.

Figure 14:
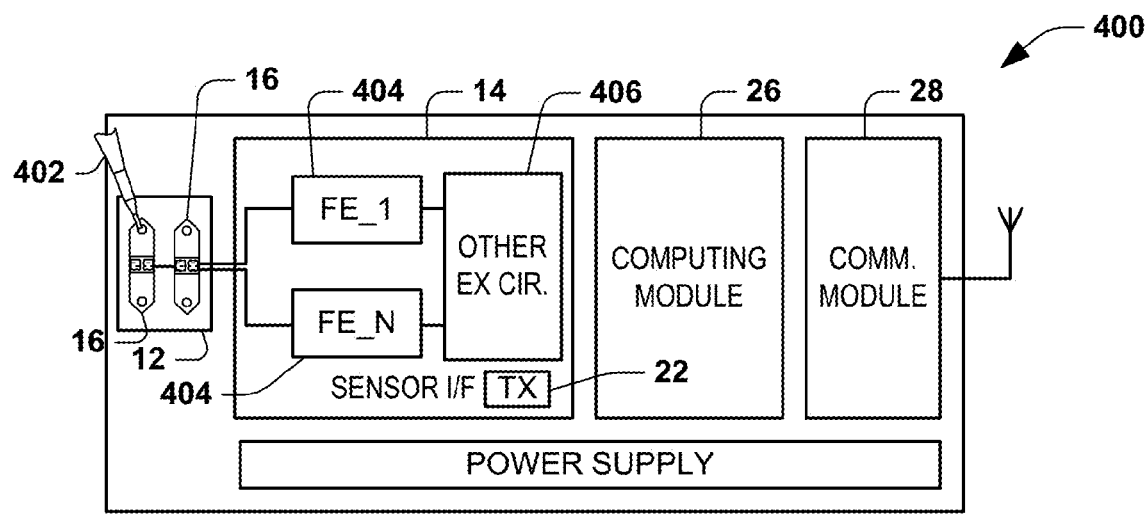
FIG. 14 is a plan view of an example DS microsystem.

As a further example, FIG. 14 depicts another example of a DS microsystem that can be implemented as an integrated palmtop system, such as within the design specifications of Table 1. Table 1 provides an example of some target performance metrics that can be implemented for a DS microsystem (e.g., the system 10 or 400; as well as the system comprising circuits 200, 300 and sensor 16. The components of the sensor can be constructed of biocompatible materials, such as including gold, glass and PMMA, commonly used in biomicrofluidic devices.

TABLE 1

SUMMARY OF EXAMPLE TARGET PERFORMANCE

Sensor - Size: 15 × 15 × 2 mm$^3$; Sample Volume: ~1 μL/channel
Interface IC - Size: 4 × 4 mm$^2$ (in 90 nm RF CMOS); Supply: 1.2 V;
Power: <100 mW
DS Microsystem - Freq: 5 MHz-10 GHz; $\Delta\varepsilon_{r,\ max}$ = 1-100 (programmable by $V_{RF}$); $\Delta\varepsilon_{r,\ min}$ = 0.001 ($\Delta\varepsilon_{r,\ max}$ = 1)

In the following description of FIG. 14, components of the system 400 are referred to using similar reference numbers refer to components previously introduced with respect to FIG. 1. The system 400 can include a sensing apparatus 12 and associated interface electronics 14. In the example of FIG. 14, the sensing apparatus 12 includes multiple DS sensors 16 (e.g., corresponding to the example sensor structure 100 of FIGS. 5 and 6). Thus, the sensor 16 and interface electronics 14 can be configured to produce a complex output that depends on (e.g., varies as a mathematical function of) the complex permittivity of fluid disposed in a microfluidic sensor channel of each DS sensor 16.

For example, a micropipette (or other device) 402 can be employed to inject a MUT into the microfluidic channel of each sensor 16. In this example, assume that the same MUT is injected into each channel. In other examples, a reference material and an MUT can be injected into channels of different sensors. The sensor interface electronics 14 includes transmitter circuitry 22 to provide an excitation signal (e.g., at single frequency or a range of one or more bands) to an input of a given sensor containing a volume of the MUT. The transmitter can provider another different excitation signal can be provided to the other DS sensor over a frequency range (e.g., one or more bands). The outputs of each sensor 16 are coupled to respective front-end RF modules 404 (demonstrated at FE_1 through FE_N, where N is a positive integer denoting the number of front end modules, which can be the same as the number of sensors) of the receiver (e.g., receiver 24). Each front-end RF module 404 is configured to preprocess (e.g., perform down-conversion, filtering and amplification) each transmitted signal received in response to an excitation signal and provide corresponding IF signals, such as disclosed with respect to FIG. 9. The IF signals from a given one of the front-end RF module 404 can be selectively provided to other receiver circuitry 406 for further processing into a system output signal (e.g., differential signal system_out+ and system_out−).

The system output signal can be converted to a digital version of the signal and provided to computing module 26. The computing module 26 can calculate permittivity for the MUT based on the system output signal to provide corresponding output data. The output data can include complex permittivity values (e.g., real and imaginary permittivity) computed over the aggregate range of excitation frequencies, including different subranges provided to each DS sensor 16. Output data can also include raw signal measurements and the input excitation frequencies. The computing module 26 can further provide the output data to a communication module 28. The communication module 28 can send the output data and raw measurement data to an external device. For example, the communication module 28 can wirelessly transmit the output data to an external device (e.g., a smartphone or tablet computer) for further data processing and/or to display the information to the user. The external device can also wirelessly transmit command information to the measurement system 400 to program one or more of the system parameters (e.g., signal gain and/or frequency range) to control its operation. The DS microsystem 400 of FIG. 14 can include a housing that contains the sensor interface electronics 14, computing module 26 and communication module 28 such that it can provide a portable, palm top structure.

The computing module 26 can also implement a calibration method (e.g., calibration method 36 or 500) that functionally relates the measured RF output of the dielectric spectroscopy microsystem 400 to the complex permittivity of the MUT in the sensor channel over a range of excitation frequencies. By way of example, FIG. 15 is a flow diagram demonstrating an example method (e.g., corresponding to calibration method 36 of FIG. 1) 500 implemented by an integrated computing system to calibrate the DS system 400. An in-circuit calibration procedure mitigates the effects of parasitic circuit elements and enables the data processing methods (e.g., data processing 34 of FIG. 1) to accurately characterize the admittance of the capacitive sensing area, Ys. The calibration method 500 can be an automated or semi-automated process in response to a user input. The calibration method 500 can be based on a linear or nonlinear fit of the sensor output characteristics loaded with reference calibration materials, each having a known complex permittivity at a known temperature and over a range of excitation frequencies. For example, the process can be performed at room temperature (or other known temperature) immediately prior to the measurement of the MUT to minimize the effects of ambient variations. In other examples, this calibration process can be performed at a plurality of different temperatures to determine the calibration coefficients over an ambient temperature range.

At 502 permittivity values for a set of reference solutions can be stored in memory. For example, the permittivity values can be measured for a set of reference solutions to characterize complex dielectric permittivity (e.g., $\in_{r,ref}'$ and $\in_{r,ref}''$ for each reference solution over a range of test frequencies. In some examples, the measurements can be part of the method 500. In other examples, the complex permittivity of a set of reference solutions can be determined a priori apart from the method 500. As an example, the measurements implemented to determine the permittivity values at 502 can be obtained using a commercially available DS device (e.g., Agilent 85070E Dielectric Probe Kit or the like) over a frequency range set according to the capabilities of the network analyzer. The range of frequencies, for example, encompass the expected range of excitation frequencies to be applied (e.g., by transmitter 22) to excite the MUT in the DS sensor disclosed herein. As a further example, the sensor system is calibrated using a plurality of six reference materials (e.g., air, isopropyl alcohol (IPA), methanol, 1:3 IPA:methanol, 1:1 IPA:methanol and 3:1 IPA:methanol). Of course, other reference solutions can be used.

At 504, a given one of the reference solutions for which permittivity was determined at 502 is loaded into the DS sensor, and the system output of the sensor is measured (e.g., by receiver 24) over a range of excitation frequencies (e.g., provided by transmitter 22). For example, the range of excitation frequencies can be the same or at least overlap with the frequency range used to characterize the complex permittivity of the reference solutions (at 502). As a further example, the measurements at 504 for a given reference solution can be obtained as a set of output voltages over a range of frequencies by operating the transmitter 22 in the I mode. Then, another set of measurements can be obtained as another set of output voltages over the range of frequencies by operating the transmitter 22 in the Q mode. As disclosed herein, system outputs measured by receiver 24 during the I mode is functionally related to the real part of dielectric permittivity (e.g., $V_{OUT,I} \sim \in_{r,ref}'$) and the system output measured during the Q mode is functionally related to the imaginary part of dielectric permittivity (e.g., $V_{OUT,Q} \sim \in_{r,ref}''$) for each respective excitation frequency.

At 506, a determination is made whether there are any additional reference solutions. If additional solutions exist (YES), the method proceeds from 506 to 508 to repeat the measurements at 504 for the next solution over a corresponding range of excitation frequencies (e.g., applied by the transmitter 22 based on controls 32 of computing system 26). There can be any number of one or more reference solutions. Once there are no more reference solutions, the method can proceed from 506 to 510.

Figure 16:
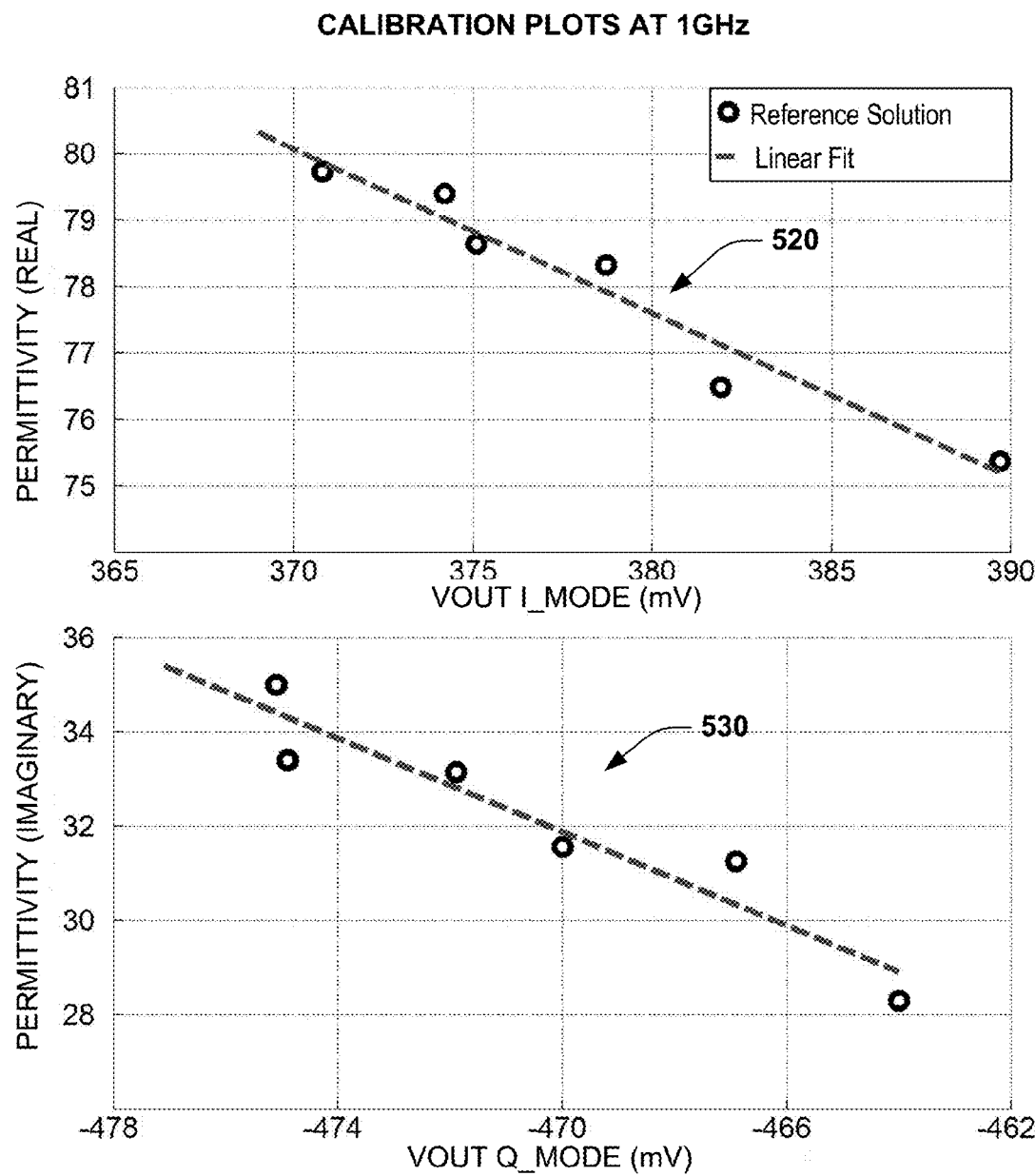
FIG. 16 is a graph demonstrating permittivity over a range of system outputs at a given excitation frequency associated with part of the example calibration method of FIG. 15.

At 510, the measured system outputs (e.g., for each of the I mode and Q mode) are fit to the real and imaginary permittivity data over a set excitation frequencies. For example, the receiver can (e.g., in response to controls 32) convert the measured output signals from the DS sensor to corresponding DC receiver outputs for each of the I and Q modes of system operation (see, e.g., receiver 200 of FIG. 9). As an example, the calibration method employs a $1^{st}$-order polynomial fit to relate the real and imaginary parts of dielectric permittivity (e.g., $\in_{r,ref}'$ and $\in_{r,ref}''$) information to I- and Q-mode measurement values $V_{OUT,I}$ and $V_{OUT,Q}$ results, respectively, corresponding to system outputs from the receiver. For example, the fitting at 510 can produce coefficients that define a linear mathematical relationship between each of the real and imaginary parts of dielectric permittivity and the DC system output voltages measured for each reference solution at a given frequency. The relationships between complex permittivity and system outputs (e.g., linear coefficients) can be determined from the fitting at 510 for each of the excitation frequencies. The fitting at 510 can be performed for each excitation frequency, for example, by computing a linear least-squares fit between the known real permittivity $\in_{r,ref}'$ of the reference calibration materials (from 502) and the $V_{OUT,I}$ measured by the sensor at 504 during the I mode. Similarly, the fitting at 510 for each excitation frequency can also compute a linear least-squares fit between the known $\in_{r,ref}''$ of the reference calibration materials (from 502) and the $V_{OUT,Q}$ measured by the sensor at 504 during the Q mode. Examples of fitting outputs to real and imaginary permittivity for an excitation frequency of 1 GHz are shown in FIG. 16. Similar linear functions can be determined for other excitation frequencies.

The resulting coefficients computed for each of a plurality of frequencies can be stored in memory to calibrate the permittivity calculator (e.g., data processing method 34), at 512. The permittivity calibration at 512 can include storing an indication of the determined (e.g., linear or non-linear) relationship between permittivity and system I and Q system outputs. For example, one or more look-up tables are programmed to provide an output of complex permittivity in response to the measured system output signal $RF_{OUT}$ for an input excitation signal at a given frequency for each of the I mode and Q mode. In other examples, the functional relationships to calibrate the permittivity calculation at 512 can be stored in other forms of data structures or mathematical functions (e.g., linear function or non-linear function) that can computed to calculate complex permittivity for a given MUT in response to the measured system output signal $RF_{OUT}$ and input excitation signal.

Based on the calibration at 512, the calibrated data processing methods can then be employed (e.g., by the data processing methods 34), at 514, to ascertain permittivity (complex relative permittivity, $\in_{r,ref}'$ and $\in_{r,ref}''$) in response to system output signals generated by receiver in response to one or more excitation signals provided to one or more DS sensor containing an MUT within the fluid channel thereof. For example, controls can operate the transmitter to provide the excitation signal for a range of one or more excitation frequencies to interrogate the MUT in the DS sensor. The receiver can be controlled (e.g., in response to controls 32) to provide respective system DC voltage outputs for each of the I mode and Q mode ($V_{OUT,I}$ and $V_{OUT,Q}$). In response to the $V_{OUT,I}$ and $V_{OUT,Q}$, which can be converted to digital values (e.g., by an ADC integrated in the interface electronics or external to the interface), the real and imaginary permittivity values can be computed for each frequency that is applied to the DS sensor, and the resulting real and imaginary permittivity values determined can be aggregated to provide a corresponding calculated complex permittivity for the MUT (at 514), such as shown in the examples of FIGS. 17 and 18.

FIG. 16 is a graph demonstrating plots 520 and 530 representing complex permittivity as a function DC system output for an excitation signal applied (e.g., by transmitter 22) as part of the calibration method of FIG. 15. In the example of FIG. 16, plots 520 and 530 show the relationship between sensor output data and permittivity for six reference materials for an excitation signal applied at 1 GHz in each of the I mode and the Q mode. In the example, of FIG. 16, the reference solutions used for sensor calibration consist of phosphate-buffered saline (PBS) plus a small amount of alcohol (10% ethanol, 5% ethanol, 2.5% ethanol, 10% methanol, 5% methanol, and 2.5% methanol). The plot 520 depicts a relationship between real permittivity of a plurality of reference solutions measured by the dielectric probe kit and DS sensor output measurements (e.g., provided by receiver 24). The other calibration plot 530 relates imaginary permittivity of the reference solutions measured by the dielectric probe kit to DS sensor measurements. In both plots 520 and 530, the dashed line shows a linear fit to the data. As mentioned, fit parameters (e.g., coefficients) can be determined for each measurement frequency and stored in memory and applied for computing complex permittivity for a given MUTs (e.g., at 514 of FIG. 15). Once the calibration coefficients are determined and used to calibrate the permittivity calculator (e.g., at 512 of FIG. 15), the permittivity calculation (at 514 of FIG. 15) can be used for any other PBS-based MUT to extract the complex permittivity information from the corresponding voltage measurements.

Figure 17:
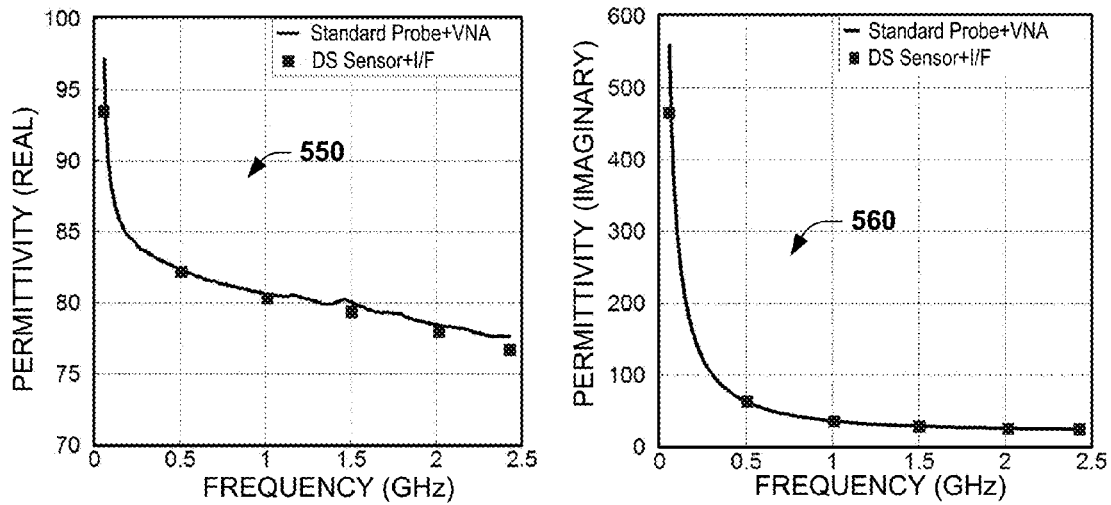
FIG. 17 is a graph demonstrating a comparison of permittivity over a range of frequencies derived from the DS system disclosed herein relative to another system.

FIG. 17 includes a graph of plots 550 and 560 demonstrating complex permittivity over a range of frequencies for a PBS reference solution. In particular, plot 550 demonstrates a comparison of real permittivity derived from a calibrated DS microsystem (e.g., 10 or 400), which is implemented according to the approach disclosed herein, compared to permittivity measurements from a standard system (e.g., a dielectric probe kit and a variable network analyzer (VNA)). Similarly, plot 560 shows a comparison of imaginary permittivity derived from a calibrated DS microsystem (e.g., 10 or 400) and permittivity measurements from the standard network analysis system. Thus, from FIG. 17, it is shown that the DS microsystem and related data processing methods disclosed herein enable accurate determination of complex permittivity over a broad range of frequencies.

Figure 18:
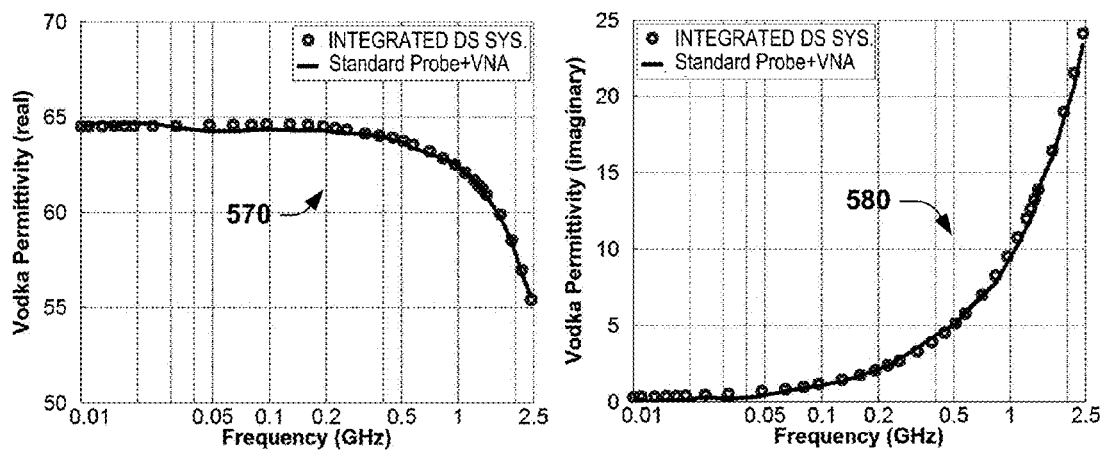
FIG. 18 is a graph demonstrating a comparison of complex permittivity over a range of frequencies derived from the integrated DS system disclosed herein relative to another system for a given MUT.

FIG. 18 depicts a graph of plots 570 and 580 demonstrating real and imaginary parts of complex relative dielectric permittivity vs. frequency for an MUT implemented as vodka (e.g., Smirnoff, 80 proof) measured by a DS system (e.g., system 10 or 400) at 32 RF excitation frequencies ranging from 10 MHz to 2.4 GHz. In this example, it is assumed that a 6-point calibration was performed with reference solutions of DI water and DI water with a small amount of alcohol (5% ethanol, 10% ethanol, 5% IPA, 10% IPA, and 20% IPA). Solid line depicts the measured curve with a standard probe (e.g., Agilent 85070E dielectric probe) interfaced with a VNA as a bulk-solution reference measurement from a typical benchtop setup.

Figure 19:
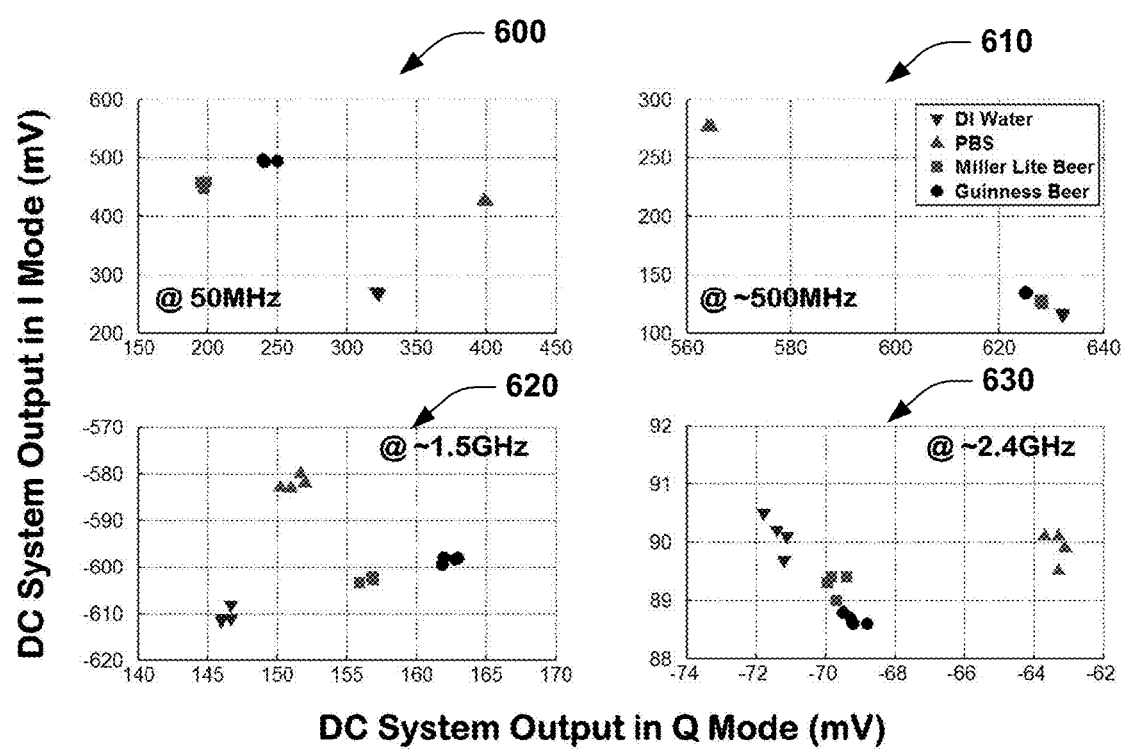
FIG. 19 is graph of system outputs in the I mode versus the Q mode such as can be used to classify a plurality of MUTs.

FIG. 19 is a graph (e.g., a classification diagram) that includes plots 600, 610, 620 and 630 of measured DC system outputs in the I mode versus DC system outputs in the Q mode over four different frequencies for a plurality of different MUTs. Graphs of the type shown in FIG. 19 can be generated by the DS system (e.g., system 10 or 400) and displayed (e.g., on device 30) to characterize a plurality of MUTs in the absence of calibration. Thus, while permittivity is not computed for each sample, the relationship between DC system outputs in each of the I and Q modes affords a relative classification among the MUTs for each different excitation frequency. In the example of FIG. 19, plot 600 shows the measured DC system output in I/Q modes at about 50 MHz, plot 610 shows the measured DC system output in I/Q modes at about 500 MHz, plot 620 shows the measured DC system output in I/Q modes at about 1.5 GHz and plot 630 shows the measured DC system output in I/Q modes at about 2.4 GHz. The measured outputs demonstrated in FIG. 19 show the respective measured DC system outputs in I/Q modes with the sensor loaded with MUTs, including DI water, phosphate-buffered saline (PBS), MILLER LITE® beer and GUINNESS® beer, as four examples of primarily-water-based MUTs. Since the dielectric relaxation characteristics of free water molecules would dominate the response at sufficiently high excitation frequencies, the MUT responses were much closer to each other at 2.4 GHz compared to 50 MHz, as evident by the much smaller dynamic range of X-Y axis. Nonetheless, a palmtop version of the DS system disclosed is fully capable of differentiating among the four MUTs across a range of frequencies.

In view of the foregoing, the DS microsystem disclosed herein thus can provide a low-power, low-cost and portable instrument for rapidly extracting key information that characterizes the molecular structure of biological solutions in a broad frequency range using μL-sample volumes, thereby paving the way for a more widespread use of DS in scientific research and clinical settings. The proposed differential measurement technique at the sensor level can be utilized to achieve high resolution in permittivity measurements by simultaneously comparing two similar solutions such as an unmodified protein solution and one that has undergone a structural change. The approach disclosed herein can also mitigate the effect of temperature-induced permittivity variation, because the temperature difference between the two biological solutions in close physical proximity would be very small. Further, planar electrodes have been widely implemented in the past due to the reduced fabrication requirements of routing all signals on a single layer. However, electric (E)-field variation near the surface of a planar electrode requires the MUT to be in direct contact with the metal electrode, because a surface coating would greatly reduce the sensitivity. The constant E-field in a parallel-plate, capacitive sensing area can solve such E-field variation.

As disclosed herein, the example parallel-plate, capacitive sensor based on a novel 3D-gap with floating electrodes (see, e.g., FIGS. 3-7) can be implemented to simultaneously achieve the advantages of a constant E-field and the reduced fabrication requirements of a single layer for signal routing. Additionally, the interface electronics (e.g., interface 14), as disclosed herein, can be implemented on a single-chip CMOS IC that integrates both sensor excitation and read-out functions for autonomous operation over a frequency range spanning >3 orders of magnitude from MHz to GHz. Further, separating the fabrication of the sensor and IC allows for sensor replacement, facilitating DS studies on potentially contaminating solutions without affecting the entire instrument.

What have been described above are examples. It is, of course, not possible to describe every conceivable combination of structures, components, or methods, but one of ordinary skill in the art will recognize that many further combinations and permutations are possible. Accordingly, the invention is intended to embrace all such alterations, modifications, and variations that fall within the scope of this application, including the appended claims.

Where the disclosure or claims recite "a," "an," "a first," or "another" element, or the equivalent thereof, it should be interpreted to include one or more than one such element, neither requiring nor excluding two or more such elements. As used herein, the term "includes" means includes but not limited to, and the term "including" means including but not limited to. The term "based on" means based at least in part on.

What is claimed is:

1. An apparatus, comprising:
an input configured to receive an input radio frequency (RF) signal;
an output to provide an output RF signal;
a fluid port; and
a capacitive sensor comprising:
co-planar sensing electrodes residing in a plane, a first of the sensing electrodes being coupled to the input and a second of the sensing electrodes coupled to the output; and
a floating electrode opposing the sensing electrodes and spaced apart from the plane of the sensing electrodes by a space that defines a fluid channel that is communicatively coupled to receive a volume of fluid material via the fluid port, the RF output signal varying in response to the input RF signal and based on a dielectric permittivity of the fluid in the fluid channel between the floating electrode and the sensing electrodes.

2. An apparatus, comprising:
an input configured to receive an input radio frequency (RF) signal;
an output to provide an output RF signal;
a fluid port; and a capacitive sensor comprising:
  substantially co-planar sensing electrodes, a first of the sensing electrodes being coupled to the input and a second of the sensing electrodes coupled to the output; and
  a floating electrode spaced apart from the sensing electrodes by a space that defines a fluid channel that is communicatively coupled to receive a fluid material via the fluid port;
  wherein the input is a first input, the RF input signal is a first RF input signal, the fluid port is a first fluid port, the fluid is a first fluid and the capacitive sensor is a first capacitive sensor, the apparatus further comprising:
  a second input configured to receive a second RF input signal that is different from the first RF input signal;
  a second fluid port; and
  a second capacitive sensor comprising:
    substantially co-planar sensing electrodes, a first of the sensing electrodes of the second capacitive sensor being coupled to the output and a second of the sensing electrodes of the second capacitive sensor being coupled to the second input; and
    a floating electrode spaced apart from the sensing electrodes of the second capacitive sensor by a space that defines another fluid channel that is communicatively coupled to receive a second fluid material via the second fluid port.

3. The apparatus of claim 2, wherein the first RF input signal and the second RF input signal form a differential RF input signal.

4. The apparatus of claim 3, further comprising an RF transmitter configured to provide the differential RF input signal to each of the first and second inputs.

5. The apparatus of claim 2, wherein the first fluid is an unknown fluid under test and the second fluid is a reference fluid having a known dielectric permittivity.

6. The apparatus of claim 1, further comprising a sensor interface system that comprises:
  a transmitter connected to provide the RF input signal to the input; and
  a receiver to receive the output RF signal from the output and to process the output RF signal and provide system output signal representing transmission characteristics of the capacitive sensor in response to the excitation signal.

7. The apparatus of claim 6, wherein the sensor interface system is an integrated circuit chip that includes the transmitter and the receiver.

8. The apparatus of claim 6, wherein the transmitter further comprises a frequency selector to select at least one frequency range to provide for the excitation signal.

9. The apparatus of claim 8, further comprising a control, responsive to a user input, to program the selector to set the at least one frequency range.

10. The apparatus of claim 8, wherein the output is a first output and the capacitive sensor is a first capacitive sensor connected between the input and the first output, the apparatus further comprising:
  at least one other capacitive sensor, each comprising:
    substantially co-planar sensing electrodes, a first of the sensing electrodes of the other capacitive sensor being coupled to the input and a second of the sensing electrodes of the other capacitive sensor being coupled to a second output; and
    a floating electrode spaced apart from the sensing electrodes of the other capacitive sensor by a space that defines another fluid channel that is communicatively coupled to receive a fluid material via a second fluid port;
  wherein the frequency selector selects a first frequency range to provide as the excitation signal for exciting the first capacitive sensor and selects an other frequency range to provide as the excitation signal for exciting the other capacitive sensor.

11. The apparatus of claim 10, wherein the receiver further comprises:
  a first front end circuit path coupled to the first output and configured to process the output signal from the first capacitive sensor according to the first frequency range; and
  a second front end circuit path coupled to the second output and configured to process the output signal from the other capacitive sensor according to the other frequency range.

12. The apparatus of claim 1, further comprising a computing module programmed to calculate an estimate of dielectric permittivity of the fluid material within the channel based on a digital representation of the RF output signal over a predetermined frequency range of the RF input signal.

13. The apparatus of claim 12, further comprising a communication module to send output data representing the estimate of dielectric permittivity to an external device via a communication link.

14. The apparatus of claim 13, wherein the communication link is a bidirectional link, the computing system being programmed to control the predetermined frequency range of the RF input signal in response to instructions received from the external device via the communication link.

15. A portable dielectric spectroscopy system, comprising:
  an integrated sensor interface system comprising:
    a transmitter configured to generate and provide a radio frequency (RF) excitation signal that varies over a range of excitation frequencies to an output for exciting a capacitive sensor containing a volume of fluid material under test; and
    a receiver coupled to at least one input to receive an input RF signal and to provide at least one system signal representing measured transmission characteristics of the capacitive sensor, which varies as a function of dielectric permittivity of the fluid material under test in response to the excitation signal over the range of excitation frequencies; and
  a computing system programmed to calculate a dielectric permittivity of the fluid material within the channel based on the at least one system signal.

16. The portable dielectric spectroscopy system of claim 15, further comprising a communication module coupled to the computing system and configured to send output data representing the estimate of dielectric permittivity to an external device via a communication link.

17. The portable dielectric spectroscopy system of claim 16, wherein the communication link is a bidirectional link, the computing system being programmed to set a frequency range of the RF input signal in response to instructions received from the external device via the communication link.

18. The portable dielectric spectroscopy system of claim 15, wherein the capacitive sensor further comprises:
  substantially co-planar sensing electrodes, a first of the sensing electrodes being coupled to the input and a second of the sensing electrodes coupled to the output; and a floating electrode spaced apart from a plane of the sensing electrodes by a space that defines a fluid channel therebetween that is communicatively coupled to receive the volume of fluid material under test via at least one fluid port.

19. The portable dielectric spectroscopy system of claim 15, wherein the capacitive sensor comprises a plurality of capacitive sensors, each including a fluid channel to receive a volume of the fluid material therein to provide each respective capacitive sensor a capacitance functionally related to a permittivity of the fluid material disposed in the fluid channel thereof.

20. The portable dielectric spectroscopy system of claim 19, wherein the receiver comprises a respective input connected to a terminal of each of the plurality of capacitive sensors to receive a corresponding input RF signal representing transmission characteristics thereof in response to the excitation signal that is provided by the transmitter to the output for each of a respective plurality of different frequency bands.

21. The portable dielectric spectroscopy system of claim 15, wherein the computing system is programmed to calibrate and control the sensor interface system for operation over a set of one or more ranges of excitation frequencies to relate the measured transmission characteristics in the corresponding processed output to the complex permittivity of the fluid material for each of the one or more ranges of excitation frequencies.

22. A method of fabricating a sensor, comprising:
forming co-planar sensor electrodes on a first substrate to provide a first part of the sensor, an electrically conductive trace extending from at least one of the sensor electrodes to a termination;
forming a floating electrode on a wall of a second substrate to provide a second part of the sensor; and
attaching the first and second parts of the sensor such that the sensor electrodes are spaced apart from and opposing the floating electrode by a gap to form a fluid channel between the floating electrode and the sensor electrodes, the gap between the floating electrode and the sensor electrodes defining a capacitive sensing area within the fluid channel between the sensor electrodes and the floating electrode.

23. The method of claim 22, wherein a pair of identical sensors are fabricated, one sensor electrode from each of the sensors being electrically connected to a common output and another sensor electrode from each of the sensors being connected to a respective one of differential inputs.

24. The method of claim 22, further comprising interposing a layer of a non-conductive material between the first and second parts of the sensor, the layer of non-conductive material including an aperture coextensive and aligned with the fluid channel in each of the first and second parts of the sensor.

25. A sensor apparatus produced according to the method of claim 22.

* * * * *

UNITED STATES PATENT AND TRADEMARK OFFICE
CERTIFICATE OF CORRECTION

PATENT NO. : 9,995,701 B2  
APPLICATION NO. : 14/728642  
DATED : June 12, 2018  
INVENTOR(S) : Pedram Mohseni Page 1 of 1

It is certified that error appears in the above-identified patent and that said Letters Patent is hereby corrected as shown below:

On the Title Page

(72) Inventors reads:
"Bakshiani"
Should read:
--Bakhshiani--

Signed and Sealed this
Second Day of October, 2018

Andrei Iancu
*Director of the United States Patent and Trademark Office*